(12) United States Patent
Stoessel et al.

(10) Patent No.: US 9,673,402 B2
(45) Date of Patent: Jun. 6, 2017

(54) PLATINUM METAL COMPLEXES WITH DIVALENT GROUPS BRIDGING TWO LIGANDS

(75) Inventors: Philipp Stoessel, Frankfurt am Main (DE); Anja Jatsch, Frankfurt am Main (DE); Esther Breuning, Ober-Ramstadt (DE)

(73) Assignee: Merck Patent GmbH (DE)

( * ) Notice: Subject to any disclaimer, the term of this patent is extended or adjusted under 35 U.S.C. 154(b) by 688 days.

(21) Appl. No.: 14/128,654

(22) PCT Filed: May 30, 2012

(86) PCT No.: PCT/EP2012/002289
§ 371 (c)(1),
(2), (4) Date: Dec. 23, 2013

(87) PCT Pub. No.: WO2013/000531
PCT Pub. Date: Jan. 3, 2013

(65) Prior Publication Data
US 2014/0110642 A1    Apr. 24, 2014

(30) Foreign Application Priority Data
Jun. 28, 2011 (EP) .................................. 11005252

(51) Int. Cl.
| C07F 15/00 | (2006.01) |
| H01L 51/00 | (2006.01) |
| C09K 11/06 | (2006.01) |
| H05B 33/14 | (2006.01) |
| H01L 51/50 | (2006.01) |

(52) U.S. Cl.
CPC ...... *H01L 51/0072* (2013.01); *C07F 15/0086* (2013.01); *C09K 11/06* (2013.01); *H01L 51/0058* (2013.01); *H01L 51/0071* (2013.01); *H01L 51/0087* (2013.01); *H05B 33/14* (2013.01); *C09K 2211/1007* (2013.01); *C09K 2211/1011* (2013.01); *C09K 2211/1014* (2013.01); *C09K 2211/1044* (2013.01); *C09K 2211/1059* (2013.01); *C09K 2211/185* (2013.01); *H01L 51/5016* (2013.01); *Y02E 10/549* (2013.01)

(58) Field of Classification Search
CPC .................................................. C07F 15/0086
See application file for complete search history.

(56) References Cited

U.S. PATENT DOCUMENTS

2011/0284799 A1* 11/2011 Stoessel .................... C07F 1/00
252/301.16
2011/0315933 A1* 12/2011 Stoessel ............... C07D 471/16
252/500

FOREIGN PATENT DOCUMENTS

| DE | WO 2010086089 A1 * | 8/2010 | ................ C07F 1/00 |
| DE | WO 2010102709 A1 * | 9/2010 | ........... C07D 471/16 |
| WO | WO-2010/086089 A1 | 8/2010 | |

OTHER PUBLICATIONS

Pettinari, Riccardo, et al., "Solid-State $^{15}$N CPMAS NMR and Computational Analysis of Ligand Hapticity in Rhodium (η-diene) Poly(pyrazolyl)borate Complexes", Inorg. Chem., vol. 49, (2010), pp. 11205-11215.
Rheingold, Arnold L., et al., "Hydrotris(indazolyl)borates" Homoscorpionates with Tunable Regiochemistry, Inorg. Chem., vol. 36, (1997), pp. 5097-5103.
International Search Report for PCT/EP2012/002289 mailed Aug. 28, 2012.

* cited by examiner

*Primary Examiner* — Francisco Tschen
(74) *Attorney, Agent, or Firm* — Drinker Biddle & Reath LLP

(57) ABSTRACT

The present invention relates to metal complexes and to electronic devices, in particular organic electroluminescent devices, comprising these metal complexes.

18 Claims, No Drawings

PLATINUM METAL COMPLEXES WITH DIVALENT GROUPS BRIDGING TWO LIGANDS

CROSS-REFERENCE TO RELATED APPLICATIONS

This application is a national stage application (under 35 U.S.C. § 371) of PCT/EP2012/002289, filed May 30, 2012, which claims benefit of European application 11005252.9, filed Jun. 28, 2011.

The present invention relates to metal complexes and to organic electroluminescent devices which comprise these metal complexes in the emitting layer.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are frequently organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters. In general, however, there is still a need for improvement in the case of OLEDs which exhibit triplet emission, in particular with respect to efficiency, operating voltage and lifetime. This also applies, in particular, to OLEDs which emit in the relatively short-wave region, i.e. green and in particular blue.

In accordance with the prior art, platinum complexes, in particular, are also employed besides iridium complexes as triplet emitters in phosphorescent OLEDs. It has been possible to achieve an improvement in these OLEDs by metal complexes with tetradentate ligands, causing the complexes to have higher thermal stability, which results in a longer lifetime of the OLEDs (WO 2005/042550).

The prior art furthermore discloses iridium complexes which contain imidazophenanthridine derivatives or diimidazoquinazoline derivatives as ligands (WO 2007/095118) and platinum complexes which contain tetradentate ligands with imidazophenanthridine or diimidazoquinazoline as part-ligands (US 2011/0073848). These complexes may result in blue phosphorescence on use in organic electroluminescent devices, depending on the structure of the ligand. Here too, further improvements with respect to efficiency, operating voltage and lifetime are still desirable. In particular, there is also still a need for improvement here with respect to the colour coordinates in order to be able to achieve deep-blue emission.

WO 2010/086089 discloses metal complexes which contain imidazo-isoquinoline derivatives as ligands. Good advances in the development of blue triplet emitters have already been achieved using complexes of this type. However, further improvements with respect to efficiency, operating voltage and lifetime are also still desirable here.

The object of the present invention is therefore the provision of novel and preferably improved metal complexes which are suitable as emitters for use in OLEDs. In particular, the object is to provide emitters which are suitable for blue- and green-phosphorescent OLEDs.

Surprisingly, it has been found that certain metal chelate complexes described in greater detail below achieve this object and result in improvements in the organic electroluminescent device, in particular with respect to the operating voltage, the efficiency and the emission colour. Particularly surprising is the result that metal complexes which contain a heteroatom as bridge V, as defined in greater detail below, have improved results compared with complexes which contain a carbon atom as bridge V. The present invention therefore relates to these metal complexes and to organic electroluminescent devices which comprise these complexes.

The invention thus relates to a compound of the formula (1),

formula (1)

where $L^1$ stands, identically or differently on each occurrence, for a part-ligand of the following formula (2),

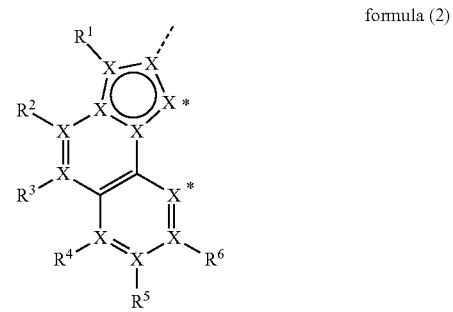

formula (2)

where the dashed bond indicates the bond to V, * denotes the position of the coordination to M and the following applies to the symbols and indices used:

M is selected from the group consisting of Pt, Ir and Au;

V is selected from the group consisting of $NR^7$, $N^-$, $BR^7$, $B(R^7)_2^-$, O, S and Se;

X is on each occurrence, identically or differently, C or N, where all X in the part-ligand of the formula (2) together form a 14π electron system, with the proviso that at least two groups X and at most 6 groups X in each part-ligand of the formula (2) stand for N;

$R^1$ to $R^6$ is on each occurrence, identically or differently, H, D, F, Cl, Br, I, $N(R^8)_2$, CN, $NO_2$, $Si(R^8)_3$, $B(OR^8)_2$, $C(=O)R^8$, $P(=O)(R^8)_2$, $S(=O)R^8$, $S(=O)_2R^8$, $OSO_2R^8$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals $R^8$, where one or more non-adjacent $CH_2$ groups may be replaced by $R^8C=CR^8$, $C\equiv C$, $Si(R^8)_2$, $C=O$, $C=S$, $C=NR^8$, $P(=O)(R^8)$, SO, $SO_2$, $NR^8$, O, S or $CONR^8$ and where one or more H atoms may be replaced by D, F, Cl, Br, I or CN, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which may be substituted by one or more radicals $R^8$, or an aralkyl or heteroaralkyl group having 5 to 60 aromatic ring atoms, which may be substituted by one or more radicals $R^8$, or a diarylamino group, diheteroarylamino group or arylheteroarylamino group having 10 to 40 aromatic ring atoms, which may be substituted by one or more radicals $R^8$; $R^4$ and $R^5$ and/or $R^5$ and $R^6$ and/or R¹ and R⁷ here may also form a mono- or polycyclic, aliphatic, aromatic and/or benzo-fused ring system with one another; furthermore, R² and R³ may form a mono- or polycyclic, aliphatic ring system with one another;

with the proviso that R¹ to R⁶ represents a free electron pair if the group X to which this radical R¹ to R⁶ is bonded is a nitrogen atom with a saturated valence;

R⁷ is on each occurrence, identically or differently, H, D, Si(R⁸)₃, C(=O)R⁸, a straight-chain alkyl or alkoxy group having 1 to 40 C atoms or an alkenyl or alkynyl group having 2 to 40 C atoms or a branched or cyclic alkyl or alkoxy group having 3 to 40 C atoms, each of which may be substituted by one or more radicals R⁸, where one or more non-adjacent CH₂ groups may be replaced by R⁸C=CR⁸, C≡C, Si(R⁸)₂, C=O, C=S, C=NR⁸, P(=O)(R⁸), SO, SO₂, NR⁸, O, S or CONR⁸ and where one or more H atoms may be replaced by D, F, Cl, Br, I or CN, or an aromatic or heteroaromatic ring system having 5 to 60 aromatic ring atoms, which may in each case be substituted by one or more radicals R⁸, or an aryloxy or heteroaryloxy group having 5 to 60 aromatic ring atoms, which may be substituted by one or more radicals R⁸, or an aralkyl or heteroaralkyl group having 5 to 60 aromatic ring atoms, which may be substituted by one or more radicals R⁸; R¹ and R⁷ here may also form a mono- or polycyclic, aliphatic, aromatic and/or benzo-fused ring system with one another;

R⁸ is on each occurrence, identically or differently, H, D, F, Cl, Br, I, N(R⁹)₂, CN, NO₂, Si(R⁹)₃, B(OR⁹)₂, C(=O)R⁹, P(=O)(R⁹)₂, S(=O)R⁹, S(=O)₂R⁹, OSO₂R⁹, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals R⁹, where one or more non-adjacent CH₂ groups may be replaced by R⁹C=CR⁹, C≡C, Si(R⁹)₂, C=O, C=S, C=NR⁹, P(=O)(R⁹), SO, SO₂, NR⁹, O, S or CONR⁹ and where one or more H atoms may be replaced by D, F, Cl, Br, I or CN, or an aromatic or heteroaromatic ring system having 5 to 60 aromatic ring atoms, which may in each case be substituted by one or more radicals R⁹, or an aryloxy or heteroaryloxy group having 5 to 60 aromatic ring atoms, which may be substituted by one or more radicals R⁹, or an aralkyl or heteroaralkyl group having 5 to 60 aromatic ring atoms, which may be substituted by one or more radicals R⁹, or a diarylamino group, diheteroarylamino group or arylheteroarylamino group having 10 to 40 aromatic ring atoms, which may be substituted by one or more radicals R⁹; two or more adjacent radicals R⁸ here may form a mono- or polycyclic, aliphatic or aromatic ring system with one another;

R⁹ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents R⁹ here may also form a mono- or polycyclic, aliphatic or aromatic ring system with one another;

L² is a bidentate part-ligand which is bonded to V;
n is 1 or 2;
m is (2-n).

Both the ligand of the complex of the formula (1) as a whole and also individual atoms X in the part-ligand of the formula (2) may also be charged.

The ligand of the complex according to the invention is a tetradentate ligand in which a bidentate part-ligand L¹ of the formula (1) and a bidentate part-ligand L² are linked to one another via a bridge V.

The part-ligand L¹ of the formula (2) is a bidentate ligand which is bonded to the metal M via one carbon atom and one nitrogen atom or via two carbon atoms or via two nitrogen atoms. If the ligand is bonded to the metal via two carbon atoms, the ligand preferably contains precisely two nitrogen atoms in the coordinating carbene ring. In a preferred embodiment of the invention, the part-ligand L¹ is bonded to the metal M via one carbon atom and one nitrogen atom.

All atoms X in the part-ligand L¹ of the formula (2) together form a 14π-electron system. Each carbon atom here contributes 1π-electron to the overall electron system. Each nitrogen atom which is only bonded in a 6-membered ring likewise contributes 1π-electron to the overall electron system. Each nitrogen atom which is bonded simultaneously in a 5-membered ring and a 6-membered ring contributes 2π-electrons to the overall electron system. Each nitrogen atom which is only bonded in a 5-membered ring contributes 1 or 2π-electrons to the overall electron system. It depends on the bonding of the nitrogen in the 5-membered ring whether this nitrogen atom contributes 1 or 2π-electrons to the overall electron system. The circle in a ring in formulae (2), (3) and (4) represents a 6π-electron system, as is usually used for the representation of aromatic or heteroaromatic structures in organic chemistry. The following structures again explain when the nitrogen contributes 1 or 2π-electrons (shown only as electrons in the scheme) to the overall π-electron system:

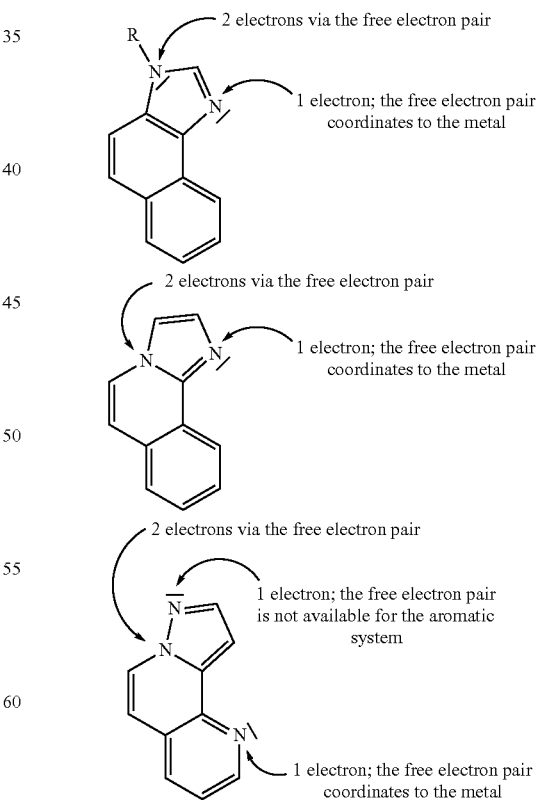

A nitrogen atom with a saturated valence in the sense of this invention is taken to mean a nitrogen atom which formally forms either one single bond and one double bond or three single bonds within the aromatic skeleton. In these cases, the radical $R^1$ to $R^6$ which is bonded to this nitrogen atom represents a free electron pair. For the purposes of this invention, a nitrogen atom with an unsaturated valence is taken to mean, by contrast, a nitrogen atom which formally only forms two single bonds within the aromatic skeleton. In these cases, the radical from $R^1$ to $R^6$ which is bonded to this nitrogen atom represents a radical as defined above and not a free electron pair. The following structures again explain what is taken to mean by a nitrogen atom with a saturated valence:

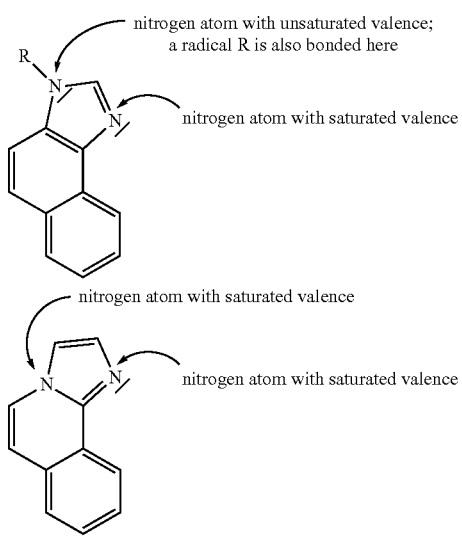

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

The ligands may also bond to the metal via a carbene carbon atom. A cyclic carbene in the sense of this invention is a cyclic group which bonds to the metal via a neutral C atom. Preference is given here to Arduengo carbenes, i.e. carbenes in which two nitrogen atoms are bonded to the carbene C atom. A five-membered Arduengo carbene ring or another unsaturated five-membered carbene ring is likewise regarded as an aryl group in the sense of this invention. In a preferred embodiment of the invention, the cyclic carbene which coordinates to the metal contains precisely two nitrogen atoms which bond to the carbene C atom, but no further nitrogen atoms.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to mean aromatic ring systems in the sense of this invention, as are systems in which two or more aryl groups are interrupted, for example, by a linear or cyclic alkyl group or by a silyl group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds of the formula (1), characterised in that these are uncharged, i.e. are electrically neutral. This is achieved in a simple manner by selecting the charge of the part-ligands $L^1$ and $L^2$ and of the bridging unit V so that they compensate for the charge of the complexed metal atom M. If the compound of the formula (1) is charged, it also contains a counterion.

In a preferred embodiment of the invention, the five-membered ring of the part-ligand $L^1$ is coordinated to the metal M via one nitrogen atom. A preferred embodiment of the part-ligand of the formula (2) is thus the structure of the following formula (3),

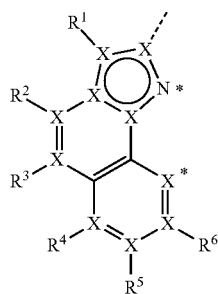

formula (3)

where the symbols used have the meanings given above and at least one symbol X and at most 5 symbols X stand for N.

In a particularly preferred embodiment of the invention, the six-membered ring of the part-ligand $L^1$ is furthermore coordinated to the metal M via a carbon atom. A particularly preferred embodiment of the part-ligand of the formula (2) and (3) is thus the structure of the following formula (4),

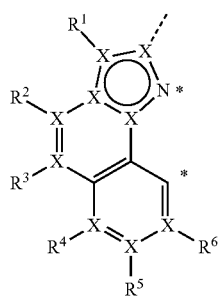

formula (4)

where the symbols used have the meanings given above and at least one symbol X and at most 5 symbols X stand for N.

In a preferred embodiment of the invention, the five-membered ring of the part-ligand of the formula (2), (3) and (4) contains at least two nitrogen atoms, where a maximum of one atom on the edge connecting the five-membered ring and the six-membered ring is a nitrogen atom. Preferred embodiments of the part-ligand of the formula (4) are the part-ligands of the following formulae (5), (6) and (7),

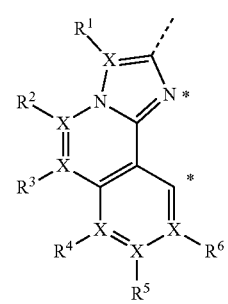

formula (5)

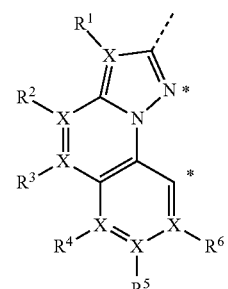

formula (6)

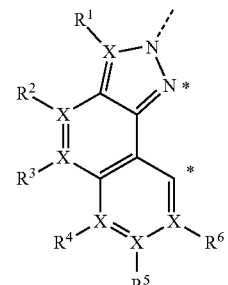

formula (7)

where the symbols used have the meanings given above and, in the case of the use of the part-ligands of the formula (7), the bridging unit V is selected from $BR^7$ and $B(R^7)_2$.

The part-ligands of the formula (5), (6) and (7) contain in total two, three, four, five or six nitrogen atoms. Preferred embodiments of the part-ligands of the formula (5) are the part-ligands of the following formulae (5a) to (5r), preferred embodiments of the part-ligands of the formula (6) are the part-ligands of the following formulae (6a) to (6r), and preferred embodiments of the part-ligands of the formula (7) are the part-ligands of the following formulae (7a) to (7r),

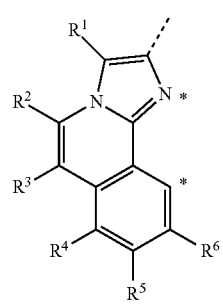

formula (5a)

formula (5b)
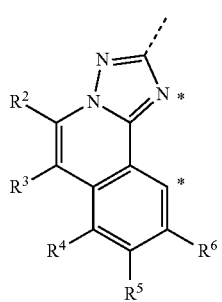
formula (5c)
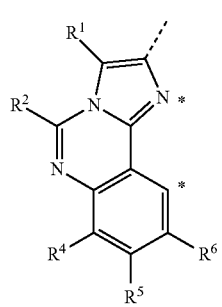
formula (5d)
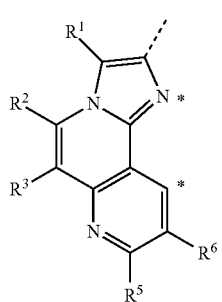
formula (5e)
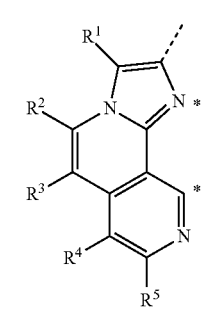
formula (5f)
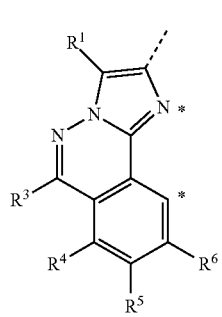
formula (5g)
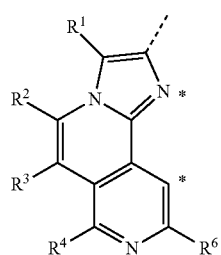
formula (5h)
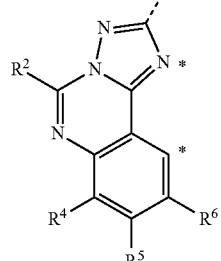
formula (5i)
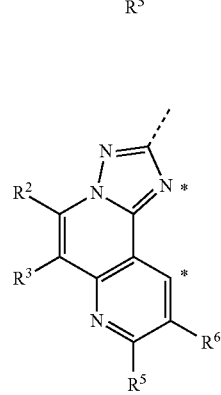
formula (5j)
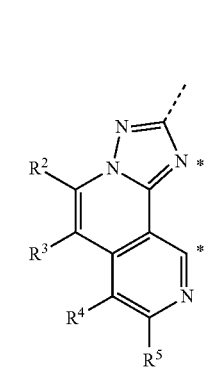
formula (5k)
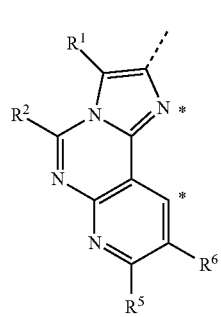

formula (5l)
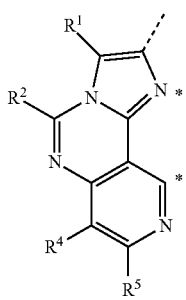
formula (5m)
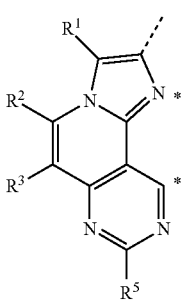
formula (5n)
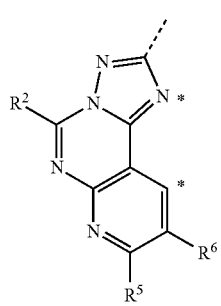
formula (5o)
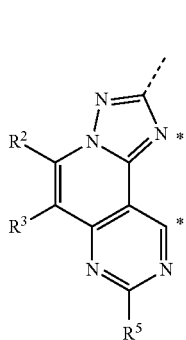
formula (5p)
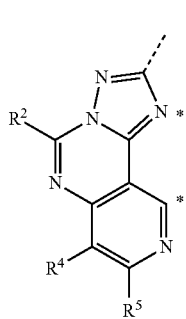
formula (5q)
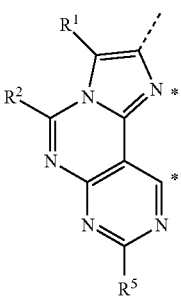
formula (5r)
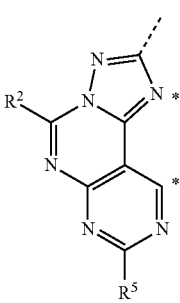
formula (6a)
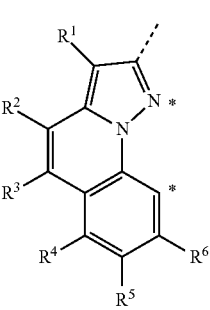
formula (6b)
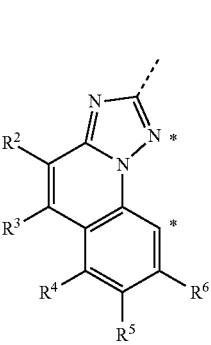
formula (6c)
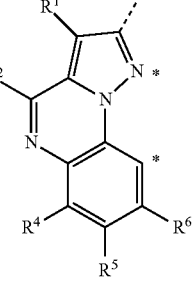

formula (6d)
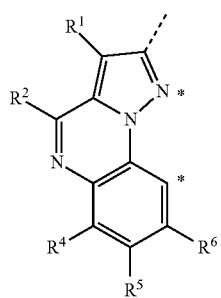
formula (6e)
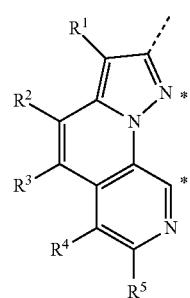
formula (6f)
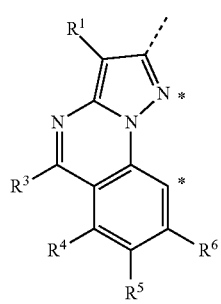
formula (6g)
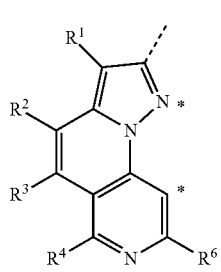
formula (6h)
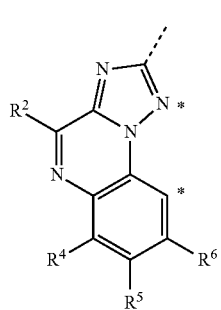
formula (6i)
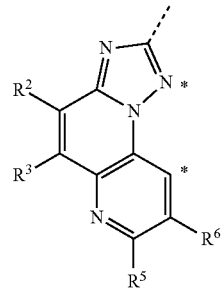
formula (6j)
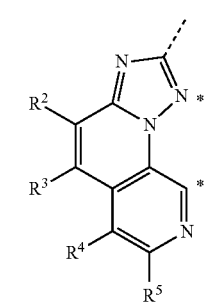
formula (6k)
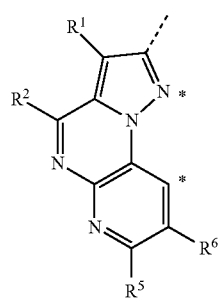
formula (6l)
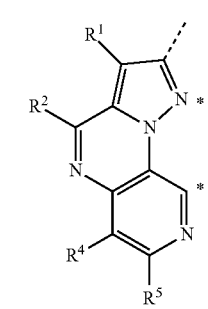
formula (6m)
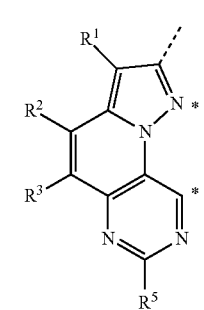

formula (6n)
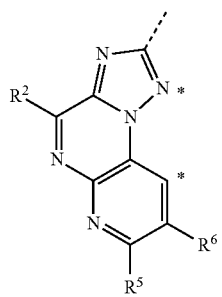
formula (6o)
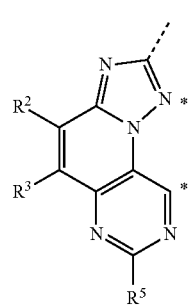
formula (6p)
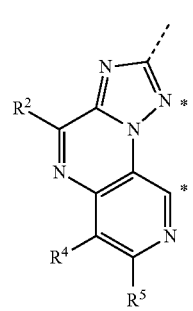
formula (6q)
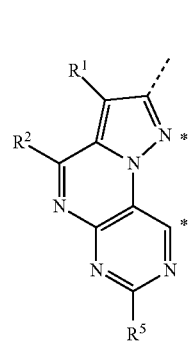
formula (6r)
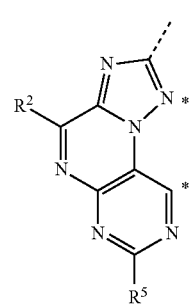
formula (7a)
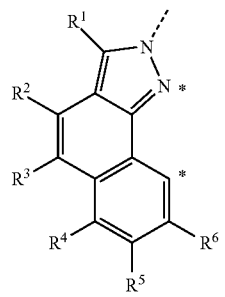
formula (7b)
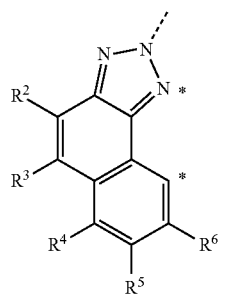
formula (7c)
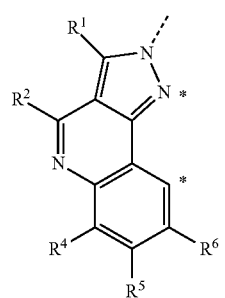
formula (7d)
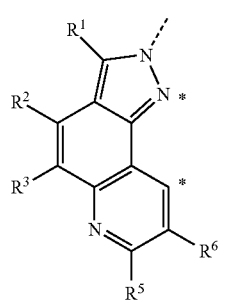
formula (7e)
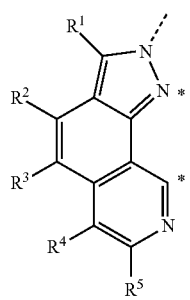

formula (7f)
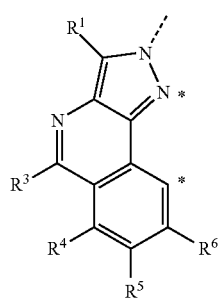
formula (7g)
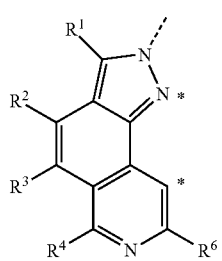
formula (7h)
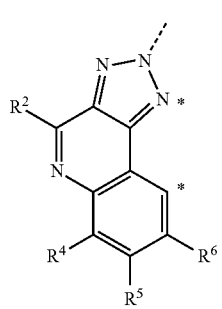
formula (7i)
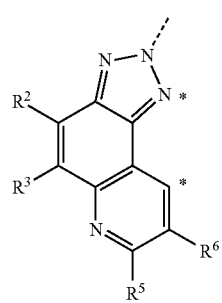
formula (7j)
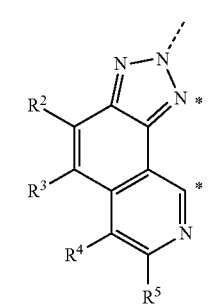
formula (7k)
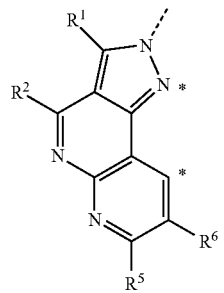
formula (7l)
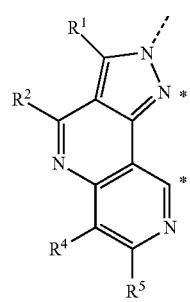
formula (7m)
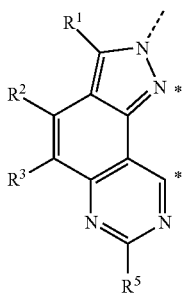
formula (7n)
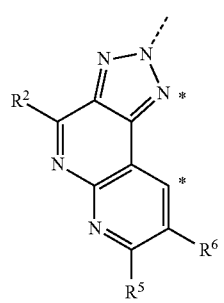
formula (7o)
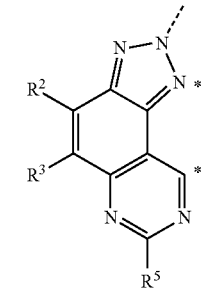

-continued formula (7p)

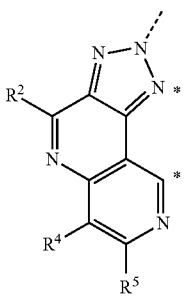

formula (7q)

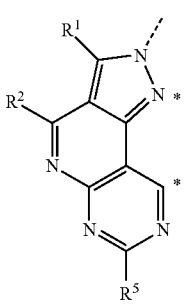

formula (7r)

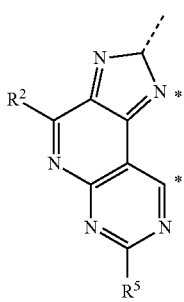

where the symbols used have the meanings given above.

The structures of the formulae (5f) and (5g) depicted above are particularly suitable for green emission, while structures (5a) to (5e) and (5h) to (5r), depending on the further part-ligands $L^2$, are also particularly suitable for blue emission. The structures of the formulae (6) and (7) are also suitable for blue and green emission.

In a preferred embodiment of the invention, the part-ligand of the formula (2), (3) and (4) contains in total 3, 4 or 5 nitrogen atoms, particularly preferably 3 or 4 nitrogen atoms, very particularly preferably 3 nitrogen atoms.

If the part-ligand of the formula (2), (3) or (4) contains three or more nitrogen atoms, it is preferred for a bulky radical to be bonded to a carbon atom which is adjacent to a nitrogen atom which is not coordinated to the metal and which is not simultaneously bonded in a five-membered ring and a six-membered ring. "Carbon atom which is adjacent to a nitrogen atom" here means that this carbon atom may be bonded directly to the nitrogen or that it is the next-possible position in which a carbon atom is present in formula (2), (3) or (4). This is explained again with reference to a specific ligand in the following diagrammatic representation:

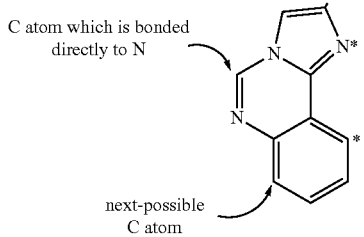

In this representation, both the carbon atom which is bonded directly to the nitrogen, and also the next-possible carbon atom if this is not bonded directly to the nitrogen, is marked. Both positions are regarded as adjacent positions to the nitrogen atom in the sense of the present application.

The bulky radical in this position is selected, identically or differently on each occurrence, from the group consisting of $N(R^8)_2$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals $R^8$, where one or more non-adjacent $CH_2$ groups may be replaced by $R^8C=CR^8$, $C≡C$, $Si(R^8)_2$, $C=O$, $C=S$, $C=NR^8$, $P(=O)$ $(R^7)$, SO, $SO_2$, $NR^8$, O, S or $CONR^8$ and where one or more H atoms may be replaced by D, F, Cl, Br, I or CN, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which may be substituted by one or more radicals $R^8$, or an aralkyl or heteroaralkyl group having 5 to 60 aromatic ring atoms, which may be substituted by one or more radicals $R^8$, or a diarylamino group, diheteroarylamino group or arylheteroarylamino group having 10 to 40 aromatic ring atoms, which may be substituted by one or more radicals $R^8$. Each of these radicals is taken to be a "bulky radical" in the sense of this application.

The bulky radical is preferably selected, identically or differently on each occurrence, from the group consisting of $CF_3$, $OCF_3$, a branched or cyclic alkyl or alkoxy group having 3 to 20 C atoms, each of which may be substituted by one or more radicals $R^8$, where one or more non-adjacent $CH_2$ groups which are not bonded directly to the ligand may be replaced by $R^8C=CR^8$, $C≡C$, $Si(R^8)_2$, $C=O$, $NR^8$, O, S or $CONR^8$ and where one or more H atoms may be replaced by D, F, Cl, Br, I or CN, or $Si(R^8)_3$, where $R^8$ is not equal to H or D, a dialkylamino group, where the alkyl groups each have 1 to 10 C atoms and may be linear, branched or cyclic, or an aromatic or heteroaromatic ring system having 5 to 60 aromatic ring atoms, which may in each case be substituted by one or more radicals $R^8$, or an aralkyl or heteroaralkyl group having 5 to 40 aromatic ring atoms, which may be substituted by one or more radicals $R^8$.

If the bulky radical stands for an alkyl group, this alkyl group then preferably has 4 to 10 C atoms. It is furthermore preferably a secondary or tertiary alkyl group in which the secondary or tertiary C atom is either bonded directly to the ligand or is bonded to the ligand via a $CH_2$ group. This alkyl group is particularly preferably selected from the structures of the following formulae (R-1) to (R-33), where the linking of these groups to the ligand is in each case also drawn in:

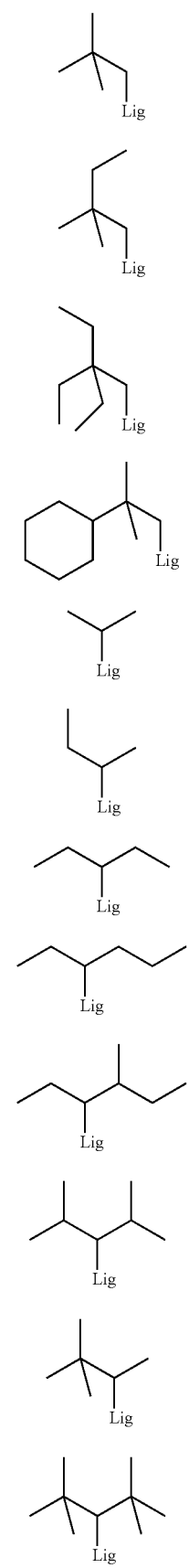
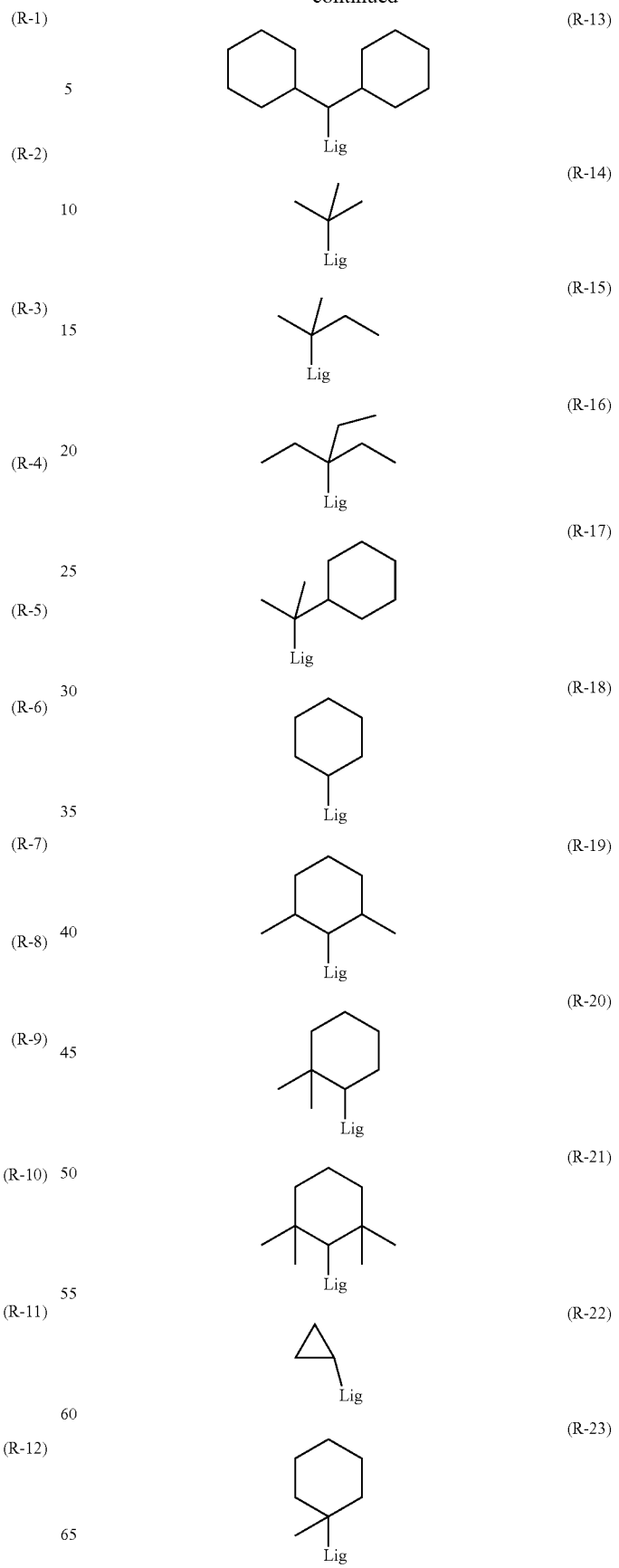

-continued
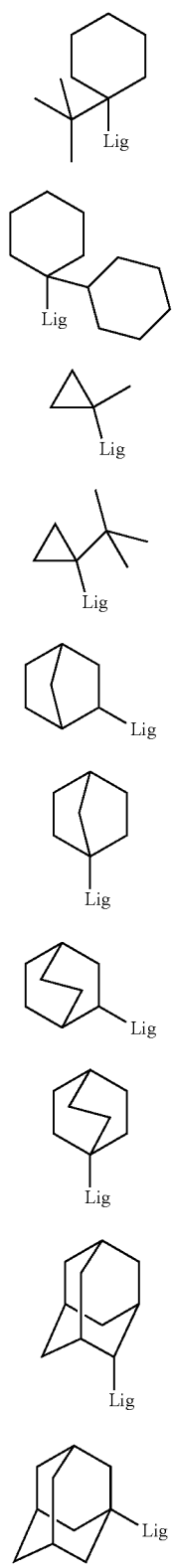
(R-24)
(R-25)
(R-26)
(R-27)
(R-28)
(R-29)
(R-30)
(R-31)
(R-32)
(R-33)
where Lig denotes the link of the alkyl group to the ligand.
If the bulky radical stands for an alkoxy group, this alkoxy group then preferably has 3 to 10 C atoms. This alkoxy group is preferably selected from the structures of the following formulae (R-34) to (R-47), where the linking of these groups to the ligand is in each case also drawn in:
(R-34)
(R-35)
(R-36)
(R-37)
(R-38)
(R-39)
(R-40)
(R-41)
(R-42)
(R-43)

-continued

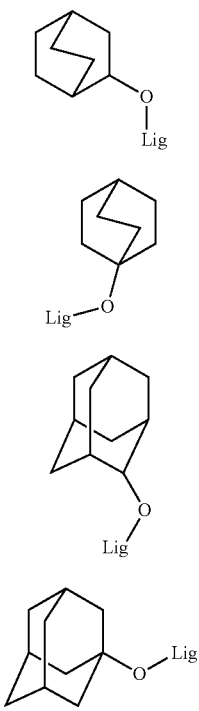

(R-44)

(R-45)

(R-46)

(R-47)

where Lig denotes the link of the alkyl group to the ligand.

If the bulky radical stands for a dialkylamino group, each of these alkyl groups then preferably has 1 to 8 C atoms, particularly preferably 1 to 6 C atoms. Examples of suitable alkyl groups are methyl, ethyl or the structures shown above as groups (R-1) to (R-33). The dialkylamino group is particularly preferably selected from the structures of the following formulae (R-48) to (R-55), where the linking of these groups to the ligand is in each case also drawn in:

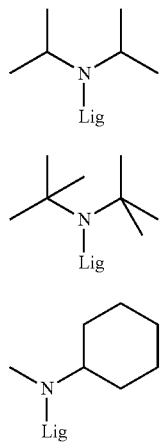

(R-48)

(R-49)

(R-50)

(R-51)

(R-52)

-continued

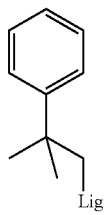

(R-53)

(R-54)

(R-55)

where Lig denotes the link of the alkyl group to the ligand.

If the bulky radical stands for an aralkyl group, this aralkyl group is then preferably selected from the structures of the following formulae (R-56) to (R-69), where the linking of these groups to the ligand is in each case also drawn in:

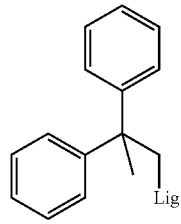

(R-56)

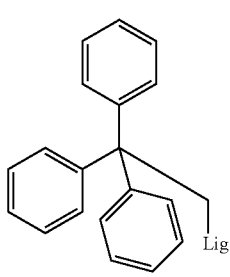

(R-57)

(R-58)

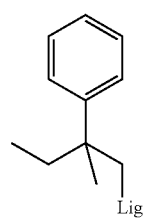

(R-59)

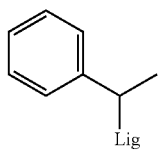 (R-60)

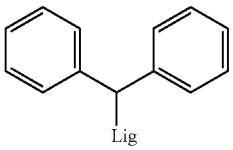 (R-61)

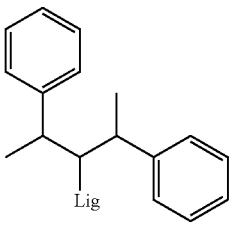 (R-62)

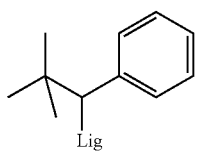 (R-63)

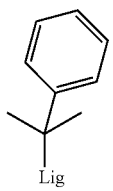 (R-64)

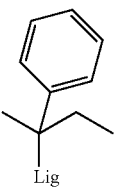 (R-65)

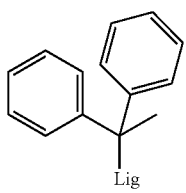 (R-66)

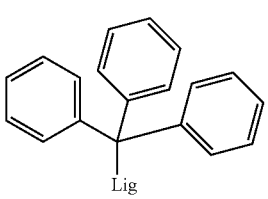 (R-67)

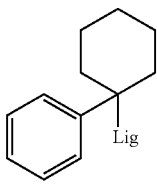 (R-68)

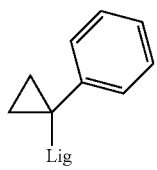 (R-69)

where Lig denotes the link of the aralkyl group to the ligand, and the phenyl groups may each be substituted by one or more radicals $R^8$.

The alkyl, alkoxy, dialkylamino and aralkyl groups may also, depending on the precise structure, have one or more stereocentres. The formation of diastereomers may thus be possible if a plurality of such alkyl, alkoxy, dialkylamino and aralkyl groups having stereocentres are present. The invention relates both to the mixtures of the various diastereomers or the corresponding racemates and also to the individual isolated diastereomers or enantiomers.

If the bulky radical stands for an aromatic or heteroaromatic ring system, this aromatic or heteroaromatic ring system then preferably has 5 to 30 aromatic ring atoms, particularly preferably 5 to 24 aromatic ring atoms. This aromatic or heteroaromatic ring system furthermore preferably contains no aryl or heteroaryl groups in which more than two aromatic six-membered rings are condensed directly onto one another. The aromatic or heteroaromatic ring system particularly preferably contains no condensed aryl or heteroaryl groups at all, and it very particularly preferably contains only phenyl groups. The aromatic ring system here is preferably selected from the structures of the following formulae (R-70) to (R-84), where the linking of these groups to the ligand is in each case also drawn in:

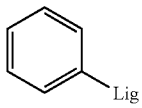 (R-70)

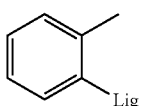 (R-71)

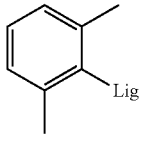 (R-72)

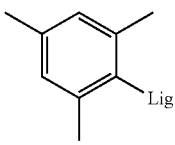 (R-73)

(R-74) 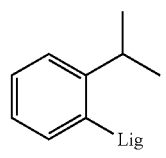

(R-75) 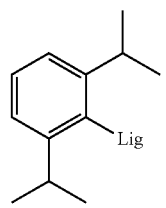

(R-76) 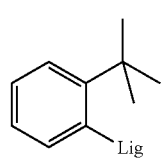

(R-77) 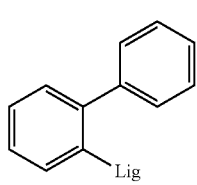

(R-78) 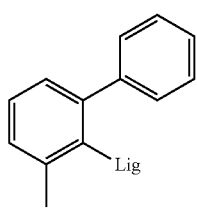

(R-79) 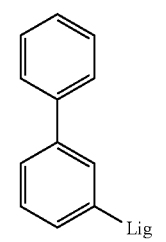

(R-80) 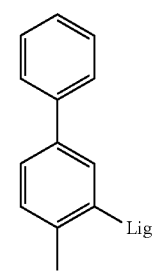

(R-81) 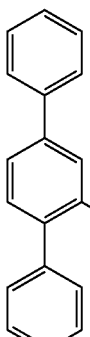

(R-82) 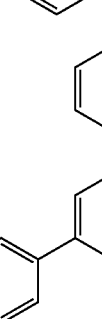

(R-83) 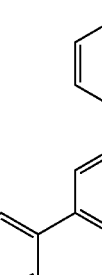

(R-84) 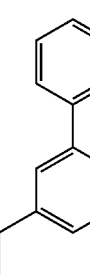

where Lig denotes the link of the aromatic or heteroaromatic ring system to the ligand, and the phenyl groups may each be substituted by one or more radicals $R^1$.

The heteroaromatic ring system is furthermore preferably selected from the structures of the following formulae (R-85) to (R-112), where the linking of these groups to the ligand is in each case also drawn in:

(R-85) 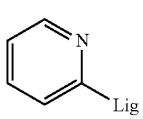

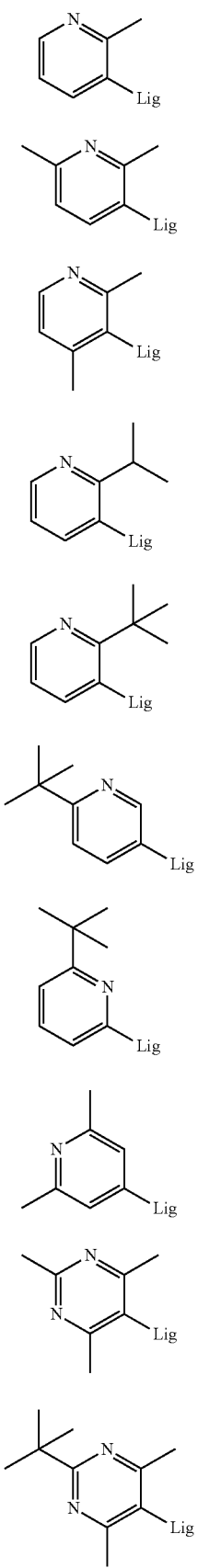
(R-86)
(R-87)
(R-88)
(R-89)
(R-90)
(R-91)
(R-92)
(R-93)
(R-94)
(R-95)
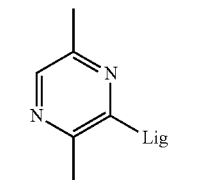
(R-96)
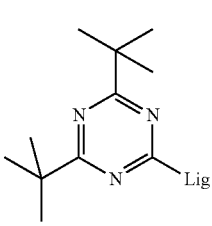
(R-97)
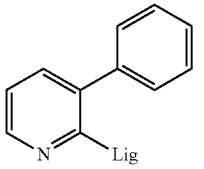
(R-98)
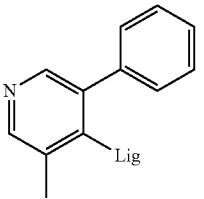
(R-99)
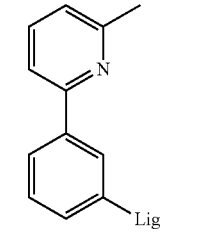
(R-100)
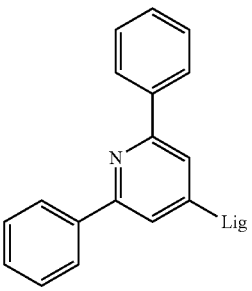
(R-101)
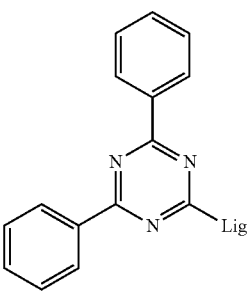
(R-102)

(R-103) 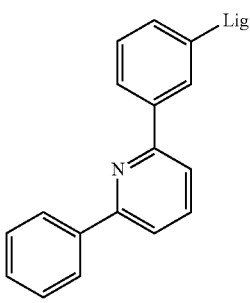

(R-104) 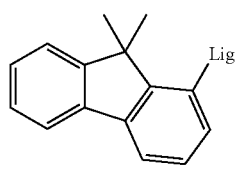

(R-105) 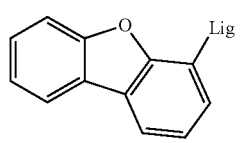

(R-106) 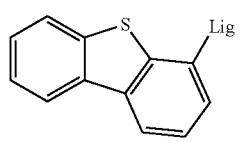

(R-107) 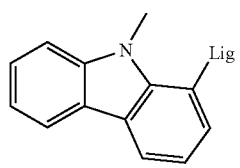

(R-108) 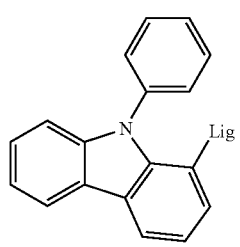

(R-109) 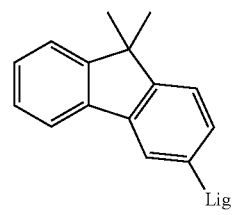

(R-110) 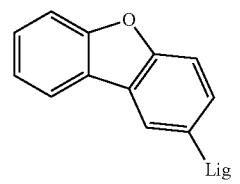

(R-111) 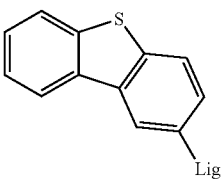

(R-112) 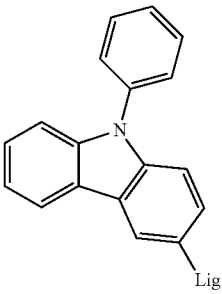

where Lig denotes the link of the aromatic or heteroaromatic ring system to the ligand, and the aromatic and heteroaromatic groups may each be substituted by one or more radicals $R^8$.

If, in addition to the above-mentioned bulky radicals, further radicals $R^1$ to $R^6$ are bonded in the moiety of the formula (2), these radicals are preferably selected on each occurrence, identically or differently, from the group consisting of H, D, F, Br, I, $N(R^8)_2$, CN, $Si(R^8)_3$, $B(OR^8)_2$, $C(=O)R^8$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^1$, where one or more H atoms may be replaced by D or F, or an aromatic or heteroaromatic ring system having 5 to 30 aromatic ring atoms, which may in each case be substituted by one or more radicals $R^8$. These radicals are particularly preferably selected on each occurrence, identically or differently, from the group consisting of H, D, F, $N(R^8)_2$, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^8$.

The index n in the complexes according to the invention is 1 or 2, i.e. the complex of the formula (1) contains one or two part-ligands of the formula (2). If n=2, the two part-ligands of the formula (2) may be identical or different. n is preferably =2. The two part-ligands of the formula (2) are then particularly preferably identical.

If n=1, the complex contains one bidentate part-ligand $L^2$. It is preferred here for the bidentate part-ligand $L^2$ to form with the metal M a cyclometallated five-membered ring or a cyclometallated six-membered ring having at least one metal-carbon bond, particularly preferably a cyclometallated five-membered ring. $L^2$ here is preferably monoanionic. In general, the combination of two groups as represented by the following formulae (8) to (35) is particularly suitable for this purpose, where one group is preferably bonded via a neutral nitrogen atom or a carbene atom and the other group is preferably bonded via a negatively charged carbon atom or a negatively charged nitrogen atom. The part-ligand $L^2$ can then be formed from the groups of the formulae (8) to (35) through these groups being bonded to one another, in each case at the position denoted by #. The position at which the groups are coordinated to the metal are denoted by *. One of the groups of the formulae (8) to (35) which form the part-ligand L² is bonded to V. This potentially present bond to V is represented by the symbol (#), with no substituent then being bonded in this position.
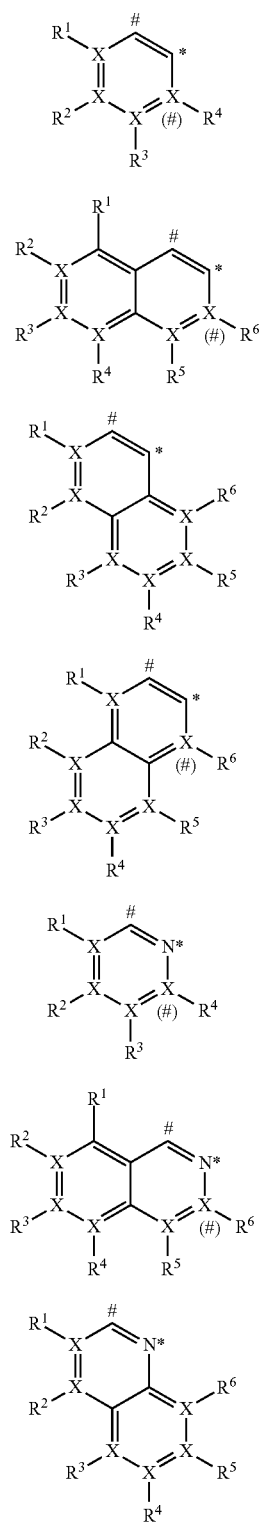
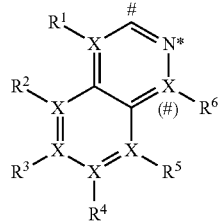
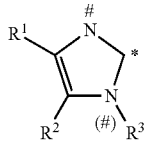
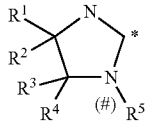
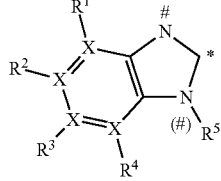
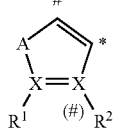
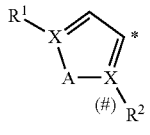
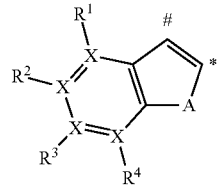
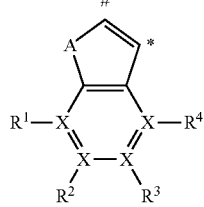
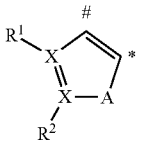

-continued formula (24)

formula (25)

formula (26)

formula (27)

formula (28)

formula (29)

formula (30)

formula (31)

formula (32)

-continued formula (33)

formula (34)

formula (35)

The symbols used here have the same meaning as described above, A stands, identically or differently on each occurrence, for O or S, and preferably a maximum of three symbols X in each group stand for N, particularly preferably a maximum of two symbols X in each group stand for N, very particularly preferably a maximum of one symbol X in each group stands for N. Especially preferably all symbols X stand for C.

Preferred radicals $R^1$ to $R^6$ in the structures of the formula (8) to (35) are selected on each occurrence, identically or differently, from the group consisting of H, D, F, Br, $N(R^8)_2$, CN, $B(OR^8)_2$, $C(=O)R^8$, $P(=O)(R^8)_2$, a straight-chain alkyl group having 1 to 10 C atoms or a straight-chain alkenyl or alkynyl group having 2 to 10 C atoms or a branched or cyclic alkyl group having 3 to 10 C atoms, each of which may be substituted by one or more radicals $R^8$, where one or more H atoms may be replaced by D or F, or an aromatic or heteroaromatic ring system having 5 to 14 aromatic ring atoms, which may in each case be substituted by one or more radicals $R^8$; adjacent radicals here, including between two of the above-mentioned groups of the formula (5) to (35), may also form a mono- or polycyclic, aliphatic, aromatic and/or benzo-fused ring system with one another. Particularly preferred radicals $R^1$ to $R^6$ are selected on each occurrence, identically or differently, from the group consisting of H, D, F, Br, CN, $B(OR^8)_2$, a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms, which may in each case be substituted by one or more radicals $R^8$; adjacent radicals here, including between two of the above-mentioned groups of the formula (5) to (35), may also form a mono- or polycyclic, aliphatic, aromatic and/or benzo-fused ring system with one another.

In a preferred embodiment of the invention, the metal M is Pt(II), Ir(I) or Au(III), particularly preferably Pt(II).

In a further preferred embodiment of the invention, the bridging unit V is selected from the group consisting of $NR^7$, O and S, particularly preferably $NR^7$.

The substituent $R^7$ here is preferably selected from the group consisting of a straight-chain alkyl group having 1 to 20 C atoms or a branched or cyclic alkyl group having 3 to 20 C atoms, each of which may be substituted by one or more radicals $R^8$, where one or more H atoms may be replaced by D, F or CN, or an aromatic or heteroaromatic ring system having 5 to 60 aromatic ring atoms, which may in each case be substituted by one or more radicals $R^8$. $R^7$ is particularly preferably selected from an aryl group which is substituted by a substituent $R^8$ other than H or D in at least one ortho-position, preferably in both ortho-positions, to the bond to N and which may likewise be substituted by substituents $R^8$ in the other positions. $R^7$ very particularly preferably stands for a phenyl group which is substituted by an alkyl group having 1 to 4 C atoms, in particular methyl, ethyl, isopropyl or tert-butyl, in at least one and preferably in both ortho-positions to the bond to the nitrogen and which may be substituted by further substituents $R^8$ at the further positions or for a linear or branched oligophenyl group having 2 to 5 phenyl groups. Particularly suitable substituents $R^7$ are selected from the groups of the following formulae (36) to (45),

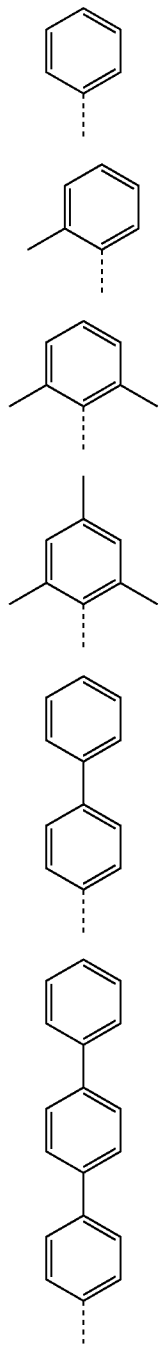

formula (36)

formula (37)

formula (38)

formula (39)

formula (40)

formula (41)

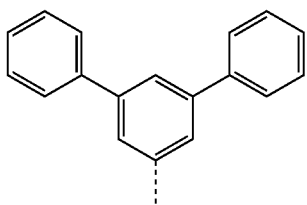

formula (42)

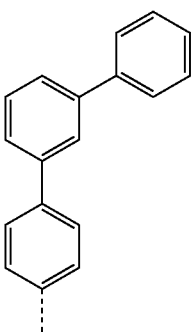

formula (43)

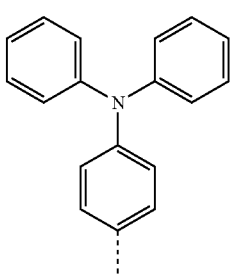

formula (44)

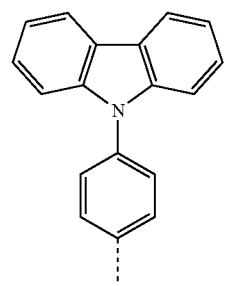

formula (45)

where the dashed bond represents the bond to the boron atom or the nitrogen atom and the terminal phenyl groups in formula (44) may also be substituted by one or more alkyl groups having 1 to 5 C atoms. Of these groups, particular preference is given to the groups the formulae (39), (40) and (45).

The preferred embodiments indicated above can be combined with one another as desired. In a particularly preferred embodiment of the invention, the preferred embodiments indicated above apply simultaneously.

The metal complexes according to the invention can in principle be prepared by various processes. However, the processes described below have proven particularly suitable.

The present invention therefore furthermore relates to a process for the preparation of the compounds of the formula (1) by reaction of the corresponding free ligands with metal alkoxides of the formula (46), with metal ketoketonates of the formula (47) or with metal halides of the formula (48), formula (46)

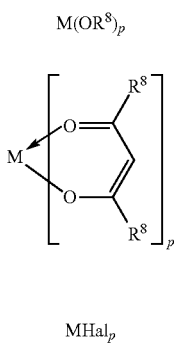

formula (47)

formula (48)

MHal$_p$ where the symbols M and R$^8$ have the meanings indicated above, Hal=F, Cl, Br or I and p stands for 1, 2 or 3, depending on the valence of the metal M.

Suitable platinum starting materials are, for example, PtCl$_2$, K$_2$[PtCl$_4$], PtCl$_2$(DMSO)$_2$, Pt(Me)$_2$(DMSO)$_2$ or PtCl$_2$(benzonitrile)$_2$. Suitable gold starting materials are, for example, AuCl$_3$, HAuCl$_4$, KAuCl$_4$ or (PPh$_3$)AuCl. Suitable iridium starting materials are, for example, [Ir(COD)Cl)]$_2$, Ir(COD)$_2$BF$_4$ or Ir(PPh$_3$)$_2$(CO)Cl.

Suitable processes for the synthesis of the complexes can be, for example, the reaction of K$_2$PtCl$_4$ with one equivalent of the ligand and an excess of about 40 equivalents of lithium acetate in glacial acetic acid or the reaction of PtCl$_2$ with one equivalent of the ligand in benzonitrile under reflux.

The synthesis here may also be activated, for example, thermally, photochemically and/or by microwave radiation. The reaction here may also be carried out in the melt without the use of an additional solvent. "Melt" here means that the ligand is in molten form and the metal precursor is dissolved or suspended in this melt.

These processes enable the compounds of the formula (1) according to the invention to be obtained in high purity, preferably greater than 99% (determined by means of $^1$H-NMR and/or HPLC).

The synthesis of the ligand precursors, the ligands and the compounds according to the invention is summarised in Scheme 1, 2 and 3.

Scheme 1:

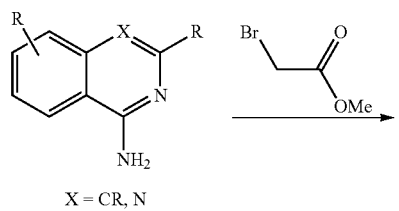

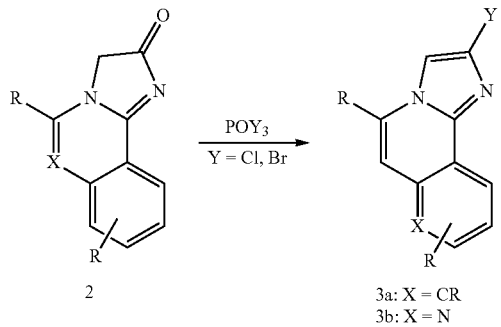

Starting from 1-aminoisoquinolines or 4-aminoquinazolines 1, reaction thereof with methyl bromoacetate gives imidazo[2,1-a]isoquinolin-2-one or imidazo[1,2-c]quinazolin-2-one 2 respectively, which can then be reacted with POCl$_3$ or POBr$_3$ to give the 2-haloimidazo[2,1-a]isoquinolines 3a or the 2-haloimidazo[1,2-c]quinazolines 3b respectively (T. A. Kuzmenko et al., Khimiya Geterotsiklicheskikh Soedinenii 1992, 12, 1698-705; C. Hamadouchi et al. Boorg. & Med. Chem. Lett. 2005, 15, 1943).

3-Substituted 2-haloimidazo[2,1-a]isoquinolines, 2-haloimidazo[1,2-c]-quinazolines, imidazo[2,1-f]-1,6-naphthyridines and 1,3a,5,6-tetraazacyclopenta[a]naphthalenes (6, 10, 14) can be prepared in accordance with Scheme 2.

Scheme 2:

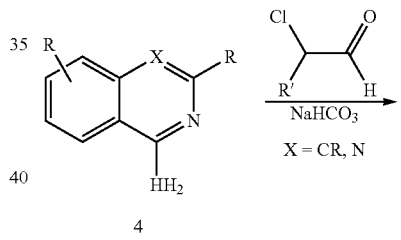

R = H, alkyl, aryl, heteroaryl, etc.
R' = alkyl, aryl, heteroaryl

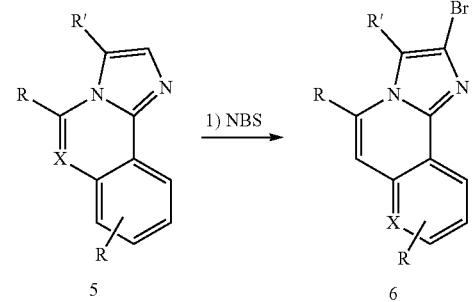

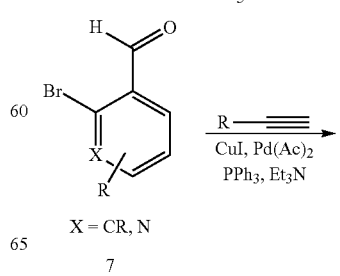

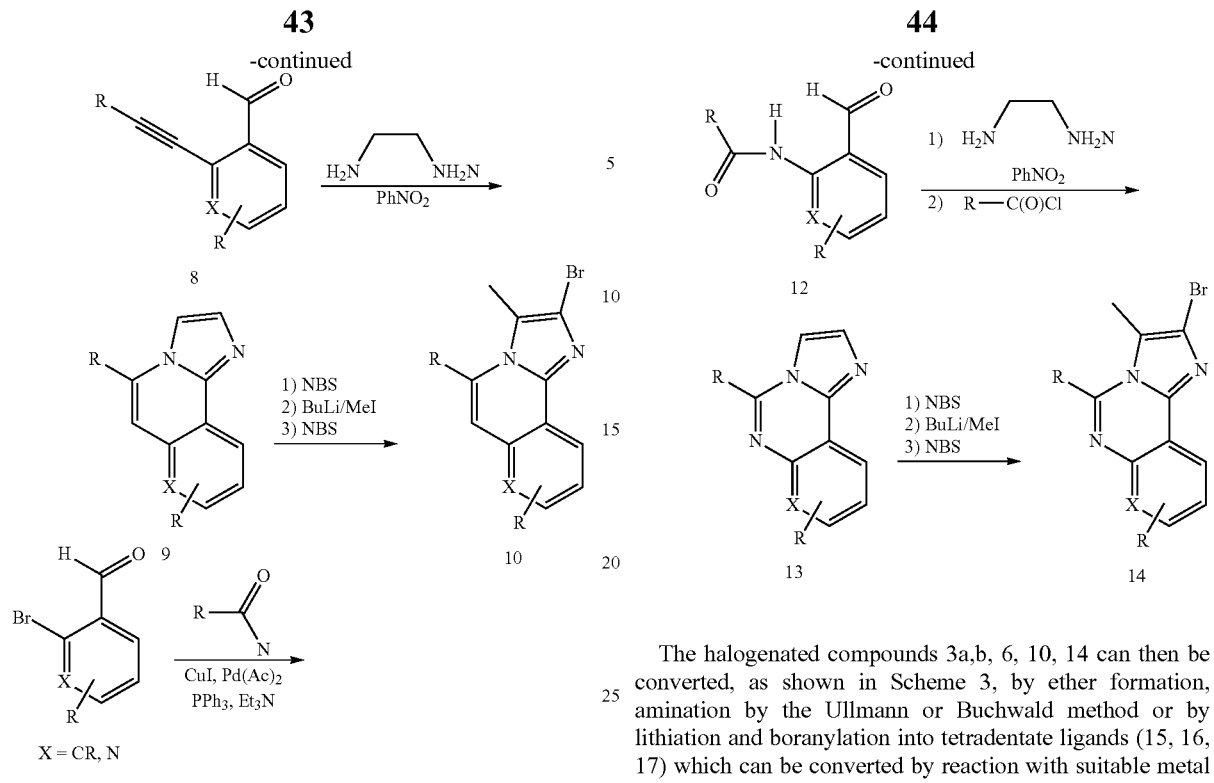
The halogenated compounds 3a,b, 6, 10, 14 can then be converted, as shown in Scheme 3, by ether formation, amination by the Ullmann or Buchwald method or by lithiation and boranylation into tetradentate ligands (15, 16, 17) which can be converted by reaction with suitable metal precursors into the complexes (18, 19, 20) according to the invention.
Scheme 3
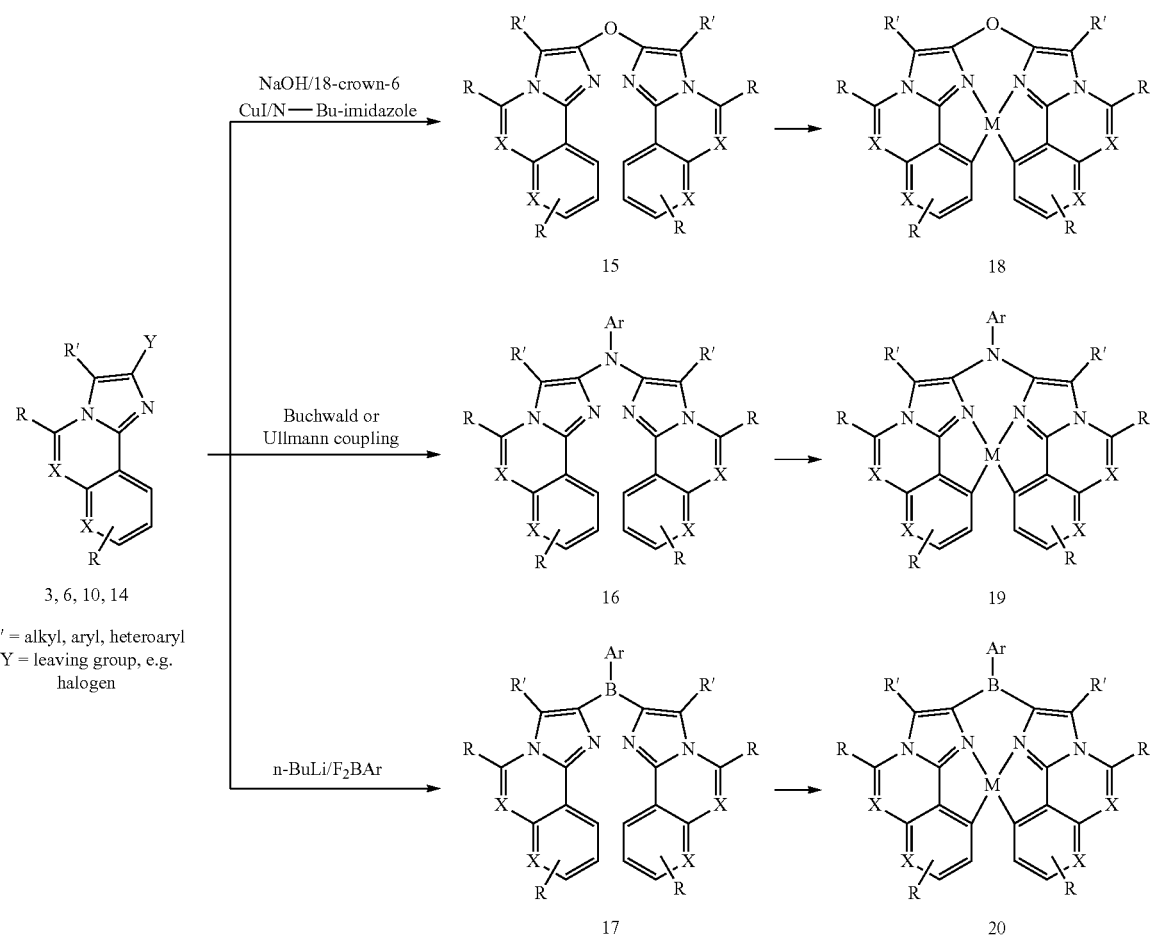

The compounds according to the invention can also be rendered soluble by suitable substitution, for example by alkyl groups, in particular branched alkyl groups, or optionally substituted aryl groups, for example, xylyl, mesityl or branched terphenyl or quaterphenyl groups.

The present invention therefore furthermore relates to a formulation, in particular a solution, suspension or miniemulsion, comprising one or more compounds of the formula (1) and at least one solvent.

The complexes of the formula (1) described above or the preferred embodiments indicated above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce.

In a preferred embodiment of the invention, the organic electroluminescent device comprises the compound of the formula (1) or the preferred embodiments indicated above as emitting compound in one or more emitting layers.

If the compound of the formula (1) is employed as emitting compound in an emitting layer, it is preferably employed in combination with one or more matrix materials. The mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula (1), based on the mixture as a whole comprising emitter and matrix material. Correspondingly, the mixture comprises between 99 and 1% by vol., preferably between 98 and 10% by vol., particularly preferably between 97 and 60% by vol., especially between 95 and 85% by vol., of the matrix material, based on the mixture as a whole comprising emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778, WO 2011/042107 or the unpublished application DE 102010005697.9.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-transporting matrix material and an electrically inert matrix material which is not involved or not essentially involved in charge transport, as described, for example, in WO 2010/108579.

It is furthermore preferred to employ a mixture of two or more triplet emitters together with a matrix. The triplet emitter having the shorter-wave emission spectrum serves as co-matrix for the triplet-emitter having the longer-wave emission spectrum. Thus, for example, the complexes of the formula (1) according to the invention can be employed as co-matrix for triplet emitters emitting at longer wavelength, for example for green- or red-emitting triplet emitters.

The compounds according to the invention can also be employed in other functions in the electronic device, for example as hole-transport material in a hole-injection or -transport layer, as charge-generation material or as electron-blocking material.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent in order either to facilitate irradiation of the organic material (O-SCs) or the coupling-out of light (OLEDs/PLEDs, O-LASERs). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are coated by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished over the prior art by the following surprising advantages:

1. Organic electroluminescent devices comprising compounds of the formula (1) as emitting materials have an excellent lifetime.

2. Organic electroluminescent devices comprising compounds of the formula (1) as emitting materials have excellent efficiency. In particular, the efficiency is significantly higher compared with analogous compounds which do not contain a structural unit of the formula (5) or formula (6).

3. By means of the metal complexes according to the invention, organic electroluminescent devices are accessible which phosphoresce in the blue colour region. Blue phosphorescence in particular can only be achieved with great difficulty in the prior art with good efficiencies and lifetimes.

These advantages mentioned above are not accompanied by an impairment of the other electronic properties.

The invention is explained in greater detail by the following examples, without wishing to restrict it thereby. The person skilled in the art will be able to produce further electronic devices on the basis of the descriptions without inventive step and will thus be able to carry out the invention throughout the range claimed.

EXAMPLES

The following syntheses are carried out, unless indicated otherwise, in dried solvents under a protective-gas atmosphere. The metal complexes are additionally handled with exclusion of light. The solvents and reagents can be purchased, for example, from Sigma-ALDRICH or ABCR. The numbers in square brackets relate to the CAS numbers of the compounds known from the literature.

A: Synthesis of Synthones S 1) 3-Methyl-6-(2,4,6-trimethylphenyl)imidazo[2,1-a]isoquinoline S1

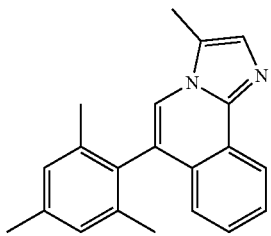 [SMILES: Cc1cc(C)c(-c2cn3c(C)cnc3c3ccccc23)c(C)c1]

1a) 4-Bromoisoquinolin-1-ylamine

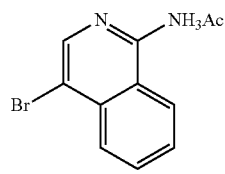

47.2 g (265 mmol) of N-bromosuccinimide are added in portions to a suspension of 36.0 g (250 mmol) of 1-aminoisoquinoline [1532-84-9] in 450 ml of glacial acetic acid, and the mixture is stirred at 20° C. for 6 h. The precipitated solid is filtered off with suction, washed twice with 100 ml of glacial acetic acid each time, twice with 100 ml of diethyl ether each time and dried in vacuo. Yield: 67.5 g (238 mmol), 95.4%. Purity: about 98% according to $^1$H-NMR.

1b) 6-Bromoimidazo[2,1-a]isoquinoline

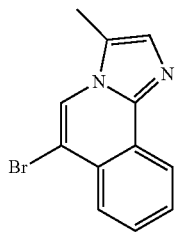

A mixture of 28.4 g (100 mmol) of 4-bromo-1-aminoisoquinoline×HAc, 25.2 ml (300 mmol) of 2-chloropropanal, 33.6 g (400 mmol) of sodium hydrogencarbonate, 300 ml of ethanol and 50 ml of water is heated under reflux for 24 h. The reaction mixture is evaporated to dryness, the residue is taken up in 300 ml of dichloromethane, the organic phase is washed twice with water and once with saturated sodium chloride solution, dried over sodium sulfate, and the solvent is removed in vacuo. The oil obtained in this way is freed from low-boiling components and non-volatile components by bulb-tube distillation in an oil-pump vacuum. Yield: 23.0 g (88 mmol) 88.0%. Purity: about 98% according to $^1$H-NMR.

1c) 6-(2,4,6-Trimethylphenyl)imidazo[2,1-a]isoquinoline, S1

A mixture of 13.1 g (50 mmol) of 6-bromoimidazo[2,1-a]isoquinoline, 24.6 g (150 mmol) of mesitylboronic acid, 53.1 g (250 mmol) of tripotassium phosphate, 4.1 g (10 mmol) of dicyclohexylphosphino-2',6'-dimethoxybiphenyl, 1.1 g (5 mmol) of palladium(II)acetate, 100 g of glass beads (diameter 3 mm) and 200 ml of toluene is stirred at 80° C. for 48 h. After cooling, the glass beads and the salts are filtered off with suction, the latter are rinsed twice with toluene, the organic phase is washed three times with 300 ml of water, dried over sodium sulfate, the toluene is then removed in vacuo, and the residue is chromatographed on silica gel with ethyl acetate:heptane. Yield: 8.5 g (28 mmol) 56.1%. Purity: about 98% according to $^1$H-NMR.

2) 5-tert-Butylimidazo[1,2-c]quinazoline, S8

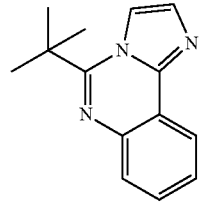 [SMILES: CC(C)(C)c1nc2ccccc2c2nccn12]

2a) N-(2-Formylphenyl)-2,2-dimethylpropionamide, S2

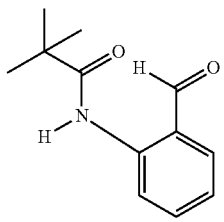

A mixture of 18.5 g (100 mmol) of 2-bromobenzaldehyde [6630-33-7], 14.2 g (140 mmol) of pivalamide [754-10-9], 81.5 g (250 mmol) of caesium carbonate, 1.7 g (3 mmol) of 9,9-dimethyl-4,5-bis(diphenylphosphino)xanthene and 630 mg (2.8 mmol) of palladium(II) acetate in 400 ml of dioxane is stirred at 100° C. for 4 h. After cooling, the solvent is removed in vacuo, the residue is taken up in 1000 ml of ethyl acetate, the organic phase is washed three times with 300 ml of water each time and once with 300 ml of saturated sodium chloride solution, filtered through a short silica-gel column, and the solvent is removed in vacuo. Yield: 18.7 g (91 mmol), 91.1%. Purity: about 95% according to $^1$H-NMR.

The following compounds are prepared analogously:

| Ex. | Starting material | Product | Yield |
|---|---|---|---|
| S3 | 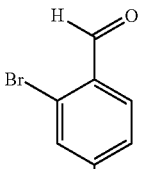 [59142-68-6] | 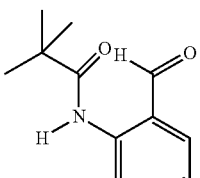 | 93% |
| S4 | 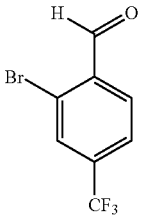 [85118-24-7] | 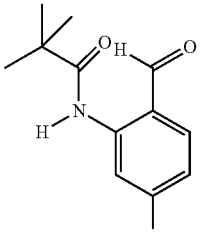 | 88% |
| S5 | 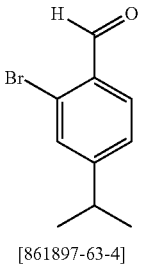 [861897-63-4] | 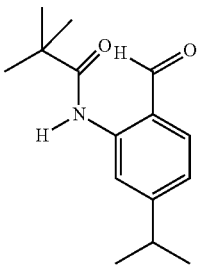 [SMILES: CC(C)c1ccc(C=O)c(NC(=O)C(C)(C)C)c1] | 90% |
| S6 | 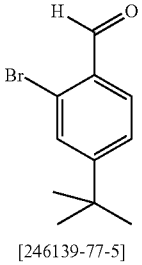 [246139-77-5] | 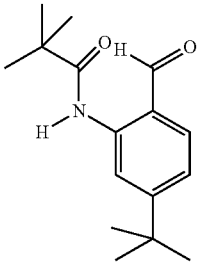 [SMILES: CC(C)(C)C(=O)Nc1cc(C(C)(C)C)ccc1C=O] | 94% |
| S7 | 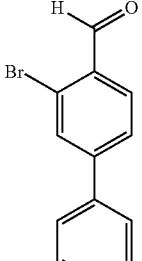 [1237125-81-3] | 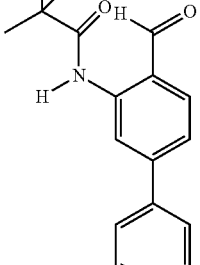 | 89% |

2b) 5-tert-Butylimidazo[1,2-c]quinazoline, S8

A mixture of 20.5 g (100 mmol) of N-(2-formylphenyl)-2,2-dimethylpropionamide, S2, 8.0 ml (120 mmol) of ethylenediamine, 50 ml of ethanol and 50 ml of nitrobenzene is stirred at room temperature for 30 min. The reaction mixture is subsequently slowly heated to 200° C., during which the ethanol, excess ethylenediamine and water distil off successively. The mixture is stirred at 200° C. for a further 6 h and allowed to cool to room temperature, during which the N-[2-(1H-imidazol-2-yl)phenyl]-2,2-dimethylpropionamide precipitates out. After removal by filtration with suction and washing with ethanol, the solid is suspended in a mixture of 150 ml of dioxane and 12.0 ml (100 mmol) of pivaloyl chloride [3282-340-2]. The suspension is heated under reflux for 20 h, cooled, added to 500 ml of ice-water, the precipitated oil is taken up in 500 ml of ethyl acetate, the organic phase is washed three times with 300 ml of water each time and once with saturated sodium chloride solution and dried over sodium sulfate. The red oil obtained after evaporation is chromatographed on aluminium oxide (basic activity grade 1) with dichloromethane. Yield: 10.6 g (47 mmol), 47.0%. Purity: about 97% according to $^1$H-NMR.

The following compounds are prepared analogously:

| Ex. | Starting material | Product | Yield |
|---|---|---|---|
| S9 | 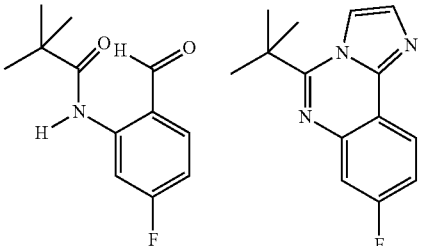 S3 | 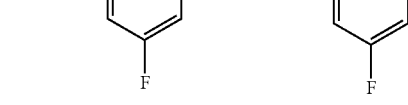 | 39% |
| S10 | 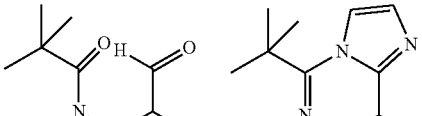 S4 | 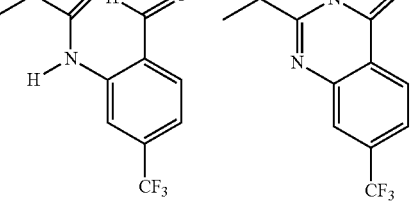 | 40% |
| S11 | 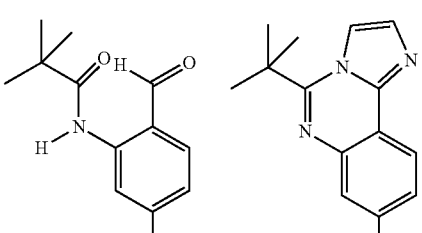 S5 | | 28% |

-continued

| Ex. | Starting material | Product | Yield |
|---|---|---|---|
| S12 | S6 | | 44% |
| S13 | S7 | | 46% |

3) 5,8-Di-tert-butylimidazo[2,1-f]-1,6-naphthyridine, S14

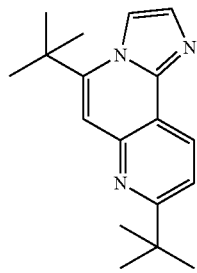 [SMILES: CC(C)(C)c1ccc2c(cc(C(C)(C)C)n3ccnc23)n1]

A mixture of 24.3 g (100 mmol) of 6-tert-butyl-2-(3,3-dimethylbut-1-ynyl)pyridine-3-carboxaldehyde (EP 10006208.2), 8.0 ml (120 mmol) of ethylenediamine and 300 ml of nitrobenzene is slowly heated to 200° C. and stirred at this temperature for 8 h. The temperature is then increased, the nitrobenzene is distilled off, and towards the end a vacuum of about 50 mbar is applied in order to remove final residues of nitrobenzene. The residue is taken up in 50 ml of dichloromethane and chromatographed on silica gel, with firstly by-products being eluted with dichloromethane and then the product being eluted with ethyl acetate. Yield: 21.2 g (75 mmol), 75.2%. Purity: about 97% according to $^1$H-NMR.

The following compounds are prepared analogously:

| Ex. | Starting material | Product | Yield |
|---|---|---|---|
| S15 | in accordance with EP 10006208.2 | | 56% |
| S16 | in accordance with EP 10006208.2 | | 68% |

| Ex. | Starting material | Product | Yield |
|---|---|---|---|
| S17 | | | 59% |
| | in accordance with EP 10006208.2 | | |
| S18 | | | 48% |
| | in accordance with EP 10006208.2 | | |

4) 4,7-Di-tert-butyl-1,3a,5,6-tetraazacyclopenta[a]naphthalene, S19

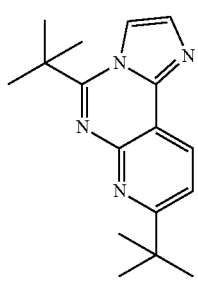 [SMILES: CC(C)(C)c1ccc2c(n1)nc(C(C)(C)C)n1ccnc21]

Procedure analogous to 2b), but using 2-N-pivaloylamido-3-cyano-6-tert-butylpyridine (in accordance with EP 10006208.2) instead of N-(2-formylphenyl)-2,2-dimethylpropionamide. Yield: 8.4 g (30 mmol), 29.7%. Purity: about 97% according to $^1$H-NMR.

5) 4,7-Di-tert-butyl-1,3a,5,8-pentaazacyclopenta[a]naphthalene, S20

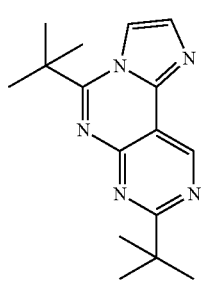 [SMILES: CC(C)(C)c1ncc2c(n1)nc(C(C)(C)C)n1ccnc21]

Procedure analogous to 2b), but using methyl 2-tert-butyl-4-(2,2-dimethyl-propynylamino)pyrimidine-5-carboxylate (in accordance with EP 10006208.2) instead of N-(2-formylphenyl)-2,2-dimethylpropionamide.

Yield: 9.2 g (32 mmol), 32.4%. Purity: about 97% according to $^1$H-NMR.

6) 5-tert-Butyl-3-methylimidazo[1,2-c]quinazoline, S21

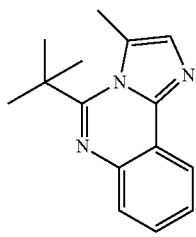 [SMILES: Cc1cnc2c3ccccc3nc(C(C)(C)C)n12]

18.8 g (105 mmol) of N-bromosuccinimide are added in portions at 20° C. to a vigorously stirred solution of 22.5 g (100 mmol) of 5-tert-butylimidazo-[1,2-c]quinazoline, S8, in 300 ml of THF. After 2 h, the THF is removed in vacuo, the residue is dissolved in 500 ml of ethyl acetate, washed three times with 300 ml of water each time and once with 300 ml of saturated sodium chloride solution. After removal of the ethyl acetate, the residue is chromatographed on silica gel with dichloromethane. The 20.0 g (66 mmol) of 5-tert-butyl-3-bromoimidazo[1,2-c]quinazoline obtained in this way are dissolved in 500 ml of diethyl ether, the solution is cooled to −78° C., 28.0 ml (70 mmol) of n-butyllithium, 2.5 M in n-hexane, are added dropwise, and the mixture is stirred for a further 15 min. 6.2 ml (100 mmol) of methyl iodide are added in one portion with vigorous stirring to the yellow suspension obtained in this way. The cooling bath is removed, and the mixture is allowed to warm slowly to room temperature, the yellow solution is washed twice with 200 ml of 5% by weight ammonia solution each time, dried over sodium sulfate, and the diethyl ether is then removed in vacuo. The residue is recrystallised from about 50 ml of cyclohexane. Yield: 8.5 g (35 mmol), 35.5%. Purity: about 97% according to $^1$H-NMR.

The following compounds are prepared analogously:

| Ex. | Starting material | Product | Yield |
|---|---|---|---|
| S22 | | | 38% |
| S23 | | | 36% |

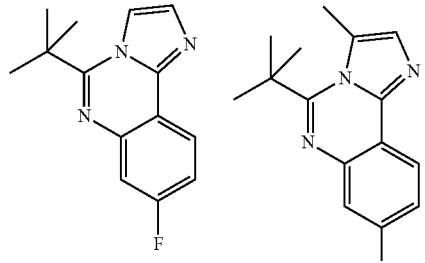

| Ex. | Starting material | Product | Yield |
|---|---|---|---|
| S24 | | | 28% |
| S25 | | | 37% |
| S26 | | | 41% |
| S27 | | | 42% |

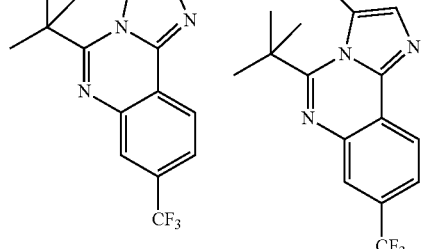

-continued

| Ex. | Starting material | Product | Yield |
|---|---|---|---|
| S28 | S15 | | 33% |
| S29 | S16 | | 36% |
| S30 | S17 | | 40% |
| S31 | S18 | | 33% |
| S32 | S19 | | 35% |

-continued

| Ex. | Starting material | Product | Yield |
|---|---|---|---|
| S33 | S20 | | 27% |

6) 2-Bromo-3-methyl-6-(2,4,6-trimethylphenyl)imidazo[2,1-a]isoquinoline, S34

A solution of 30.0 g (100 mmol) of 3-methyl-6-(2,4,6-trimethylphenyl)-imidazo[2,1-a]isoquinoline, S1, in 200 ml of DMF is slowly added dropwise to a vigorously stirred solution of 18.8 g (105 mmol) of N-bromosuccinimide in 400 ml of DMF. The mixture is stirred for a further 1 h, the DMF is then removed in vacuo, and the residue is recrystallised from ethyl acetate/methanol. Yield: 22.9 g (60 mmol), 60.4%. Purity: about 97% according to $^1$H-NMR.

| Ex. | Starting material | Product | Yield |
|---|---|---|---|
| S35 | in accordance with WO 2010/086089 | | 45% |

| Ex. | Starting material | Product | Yield |
|---|---|---|---|
| S36 | 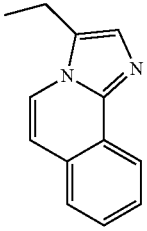 | 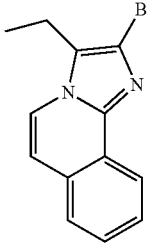 | 48% |
| | in accordance with WO 2010/086089 | | |
| S37 | 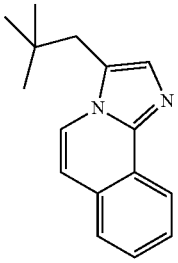 | 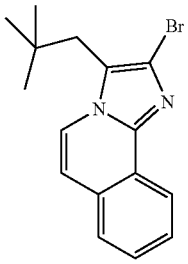 [SMILES: CC(C)(C)Cc1c(Br)nc2c3ccccc3ccn12] | 37% |
| | in accordance with WO 2010/086089 | | |
| S38 | 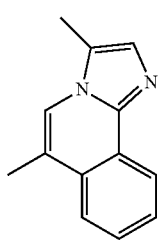 | 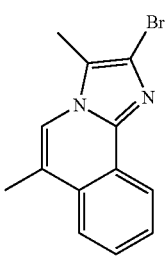 [SMILES: Cc1cn2c(C)c(Br)nc2c2ccccc12] | 45% |
| | in accordance with WO 2010/086089 | | |
| S39 | 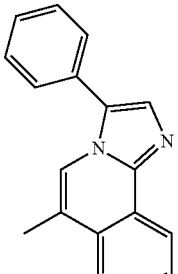 | 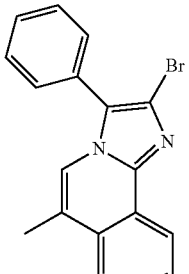 | 51% |
| | in accordance with WO 2010/086089 | | |
| S40 | 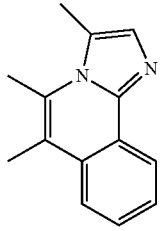 | 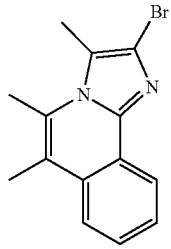 [SMILES: Cc1c(C)n2c(C)c(Br)nc2c2ccccc12] | 56% |
| | in accordance with WO 2010/086089 | | |
| S41 | 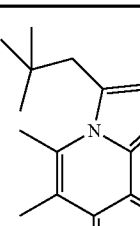 | 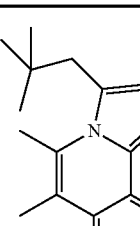 | 33% |
| | in accordance with WO 2010/086089 | | |
| S42 |  |  | 52% |
| | in accordance with WO 2010/086089 | | |
| S43 |  |  | 46% |
| | in accordance with WO 2010/086089 | | |
| S44 |  |  | 58% |
| | in accordance with WO 2010/086089 | | |

| Ex. | Starting material | Product | Yield |
|---|---|---|---|
| S45 | 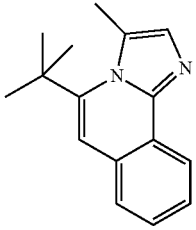 in accordance with WO 2010/086089 | 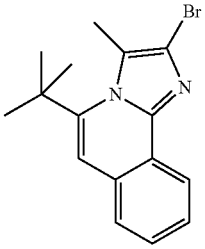 [SMILES: Cc1c(Br)nc2c3ccccc3cc(C(C)(C)C)n12] | 45% |
| S46 | 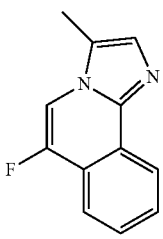 in accordance with WO 2010/086089 | 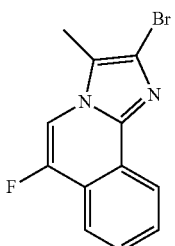 | 49% |
| S47 | 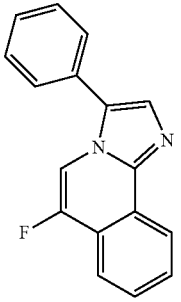 in accordance with WO 2010/086089 | 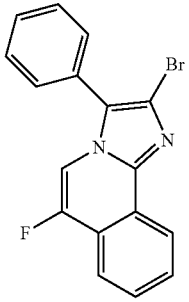 | 55% |
| S48 | 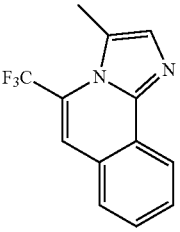 in accordance with WO 2010/086089 | 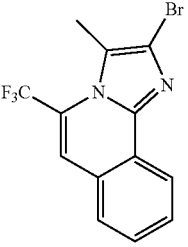 | 34% |
| S49 | 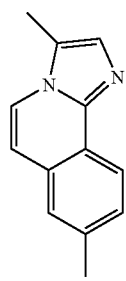 in accordance with WO 2010/086089 | 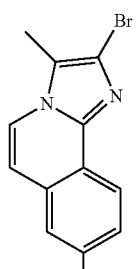 | 50% |
| S50 | 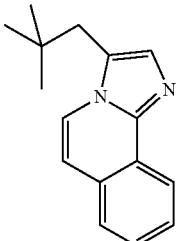 in accordance with WO 2010/086089 | 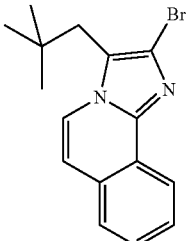 | 31% |
| S51 | 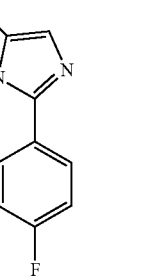 in accordance with WO 2010/086089 | 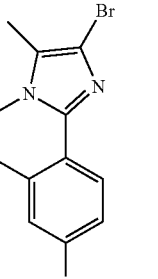 | 47% |
| S52 | 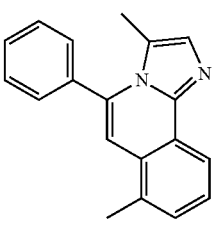 in accordance with WO 2010/086089 | 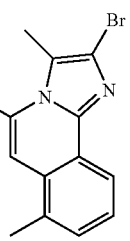 | 44% |
| S53 | 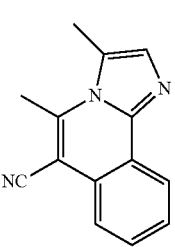 in accordance with WO 2010/086089 | 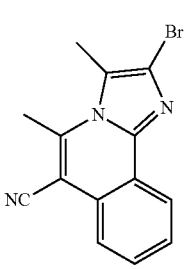 [SMILES: Cc1c(Br)nc2c3ccccc3c(C#N)c(C)n12] | 42% |

| Ex. | Starting material | Product | Yield |
|---|---|---|---|
| S54 | (in accordance with WO 2010/086089) | | 38% |
| S55 | (in accordance with WO 2010/086089) | | 40% |
| S56 | (in accordance with WO 2010/086089) | | 45% |
| S57 | (in accordance with WO 2010/086089) | | 46% |
| S58 | S21 | | 48% |
| S59 | S22 | | 45% |
| S60 | S23 | | 51% |
| S61 | S24 | | 44% |
| S62 | S25 | | 46% |

-continued
| Ex. | Starting material | Product | Yield |
|---|---|---|---|
| S63 | 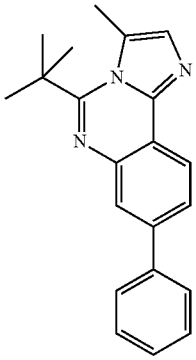 S26 | 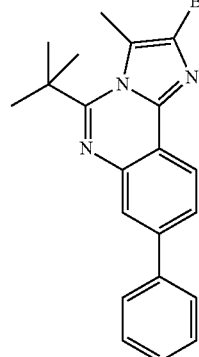 | 52% |
| S64 | 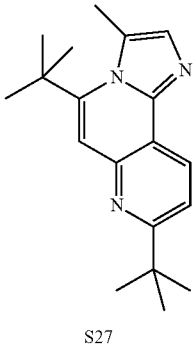 S27 | 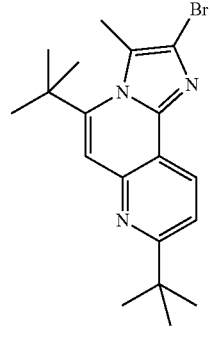 [SMILES: Cc1c(Br)nc2c3ccc(C(C)(C)C)nc3cc(C(C)(C)C)n12] | 55% |
| S65 | 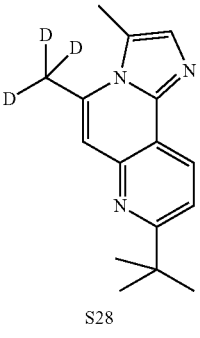 S28 | 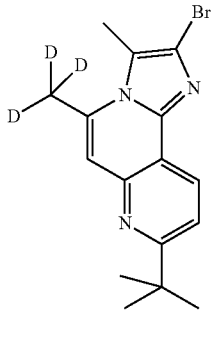 | 57% |
| S66 | 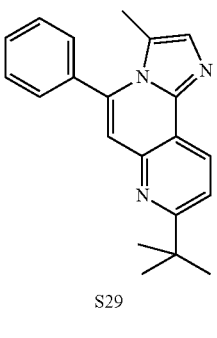 S29 | 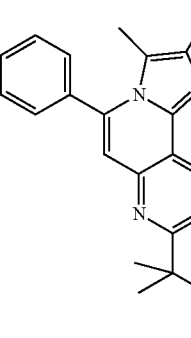 | 53% |
-continued
| Ex. | Starting material | Product | Yield |
|---|---|---|---|
| S67 | 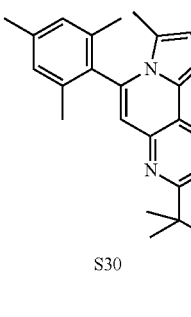 S30 | 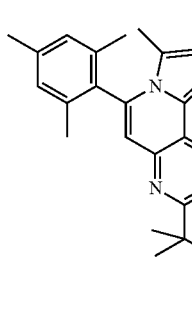 | 41% |
| S68 | 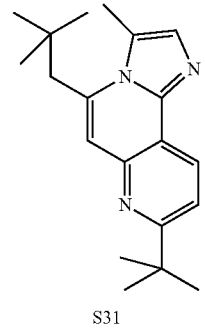 S31 | 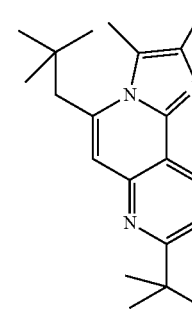 | 37% |
| S69 | 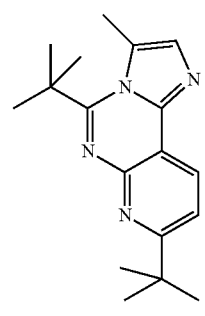 S32 | 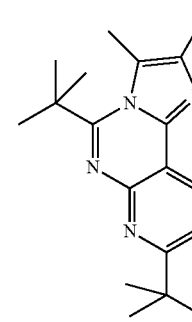 | 50% |
| S70 | 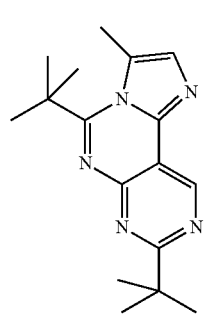 S33 | 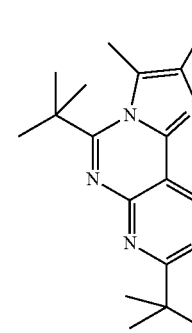 | 61% |

7) 2-Bromoimidazo[2,1-a]isoquinoline, S71

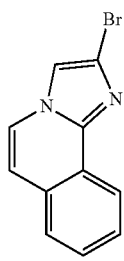

A mixture of 14.4 g (100 mmol) of 1-aminoisoquinoline [1532-84-9], 15.3 g (100 mmol) of methyl 2-bromoacetate [96-32-2], 15.2 ml (110 mmol) of triethylamine and 150 ml of ethanol is heated under reflux for 8 h. After cooling, the precipitated solid is filtered off, washed once with 40 ml of ethanol and dried in vacuo. 57.3 g (200 mmol) of phosphoryl bromide are added to the imidazo[2,1-a]isoquinolin-2-one obtained in this way, and the mixture is heated at 100° C. for 5 h. After cooling, the melt is diluted with 500 ml of toluene, 500 g of ice-water are added with vigorous stirring, and the mixture is rendered weakly alkaline using 5% NaOH. The organic phase is separated off, washed with water and dried over sodium sulfate. After removal of the solvent in vacuo, the residue is chromatographed on silica gel with dichloromethane. Yield: 18.7 g (76 mmol), 75.7%. Purity: about 96% according to $^1$H-NMR.

The following compounds are prepared analogously:

| Ex. | Starting material | Product | Yield |
|---|---|---|---|
| S72 | 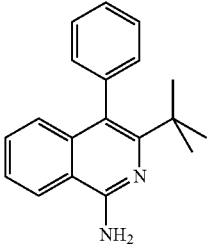 in accordance with WO 2010/086089 | 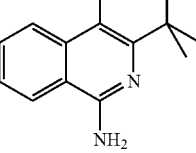 | 70% |
| S73 | 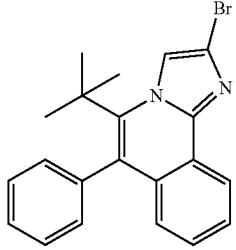 [SMILES: CC(C)(C)c1c(-c2ccccc2)c2ccccc2c2nc(Br)cn12] in accordance with WO 2010/086089 | 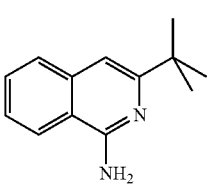 | 73% |
| S74 | 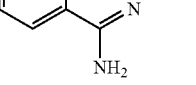 in accordance with WO 2010/086089 | 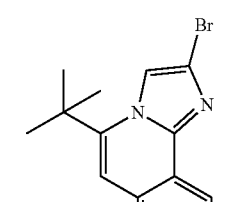 | 64% |
| S75 | 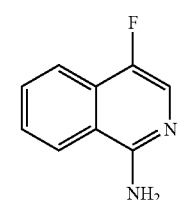 in accordance with WO 2010/086089 | 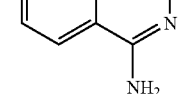 | 74% |
| S76 | 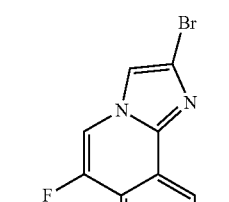 in accordance with WO 2010/086089 | 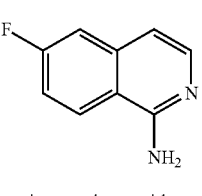 | 68% |
| S77 | 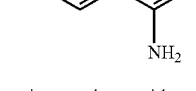 in accordance with WO 2010/086089 | 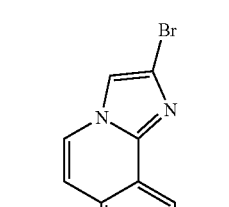 | 62% |
| S78 | 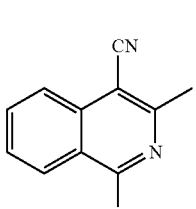 in accordance with WO 2010/086089 | 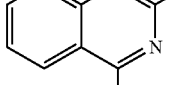 | 31% |

| Ex. | Starting material | Product | Yield |
|---|---|---|---|
| S79 | 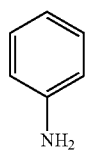 in accordance with WO 2010/086089 | 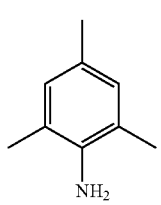 | 66% |

B: Synthesis of Ligands L

1) Ligands where V=NR

A mixture of 100 mmol of the bromide, 50 mmol of the aniline/amine, 12.5 g (130 mmol) of sodium tert-butoxide, 10.0 ml (10 mmol) of tri-tert-butylphosphine, 1 M in toluene, and 1.1 g (5 mmol) of palladium(II) acetate in 300 ml of toluene is heated under reflux for 24 h. After cooling, the organic phase is washed twice with 200 ml of water each time, dried over sodium sulfate, the toluene is removed in vacuo, the residue is chromatographed on silica gel with ethyl acetate/heptane, and the solid is subsequently freed from readily volatile and non-volatile components by fractional sublimation (p about $10^{-5}$ mbar, T about 260-300° C.). Purity: about 99% according to $^1$H-NMR.

The following anilines/amines are used:

[62-53-3]

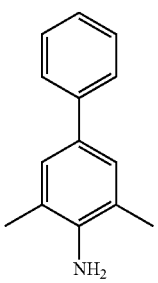

[88-05-1]

[54810-82-1]

[106-49-0]

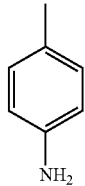

[769-92-6]

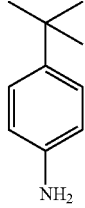

[92-67-1]

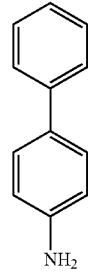

[75-64-9]

[504-24-5]

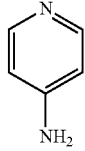

[52708-37-9]

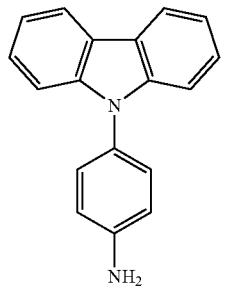

[59950-55-9]

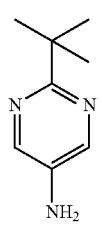

-continued
[2380-36-1]
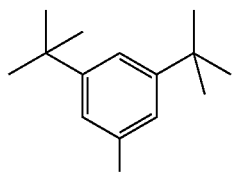
[2243-30-3]
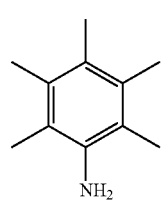
[371-40-4]
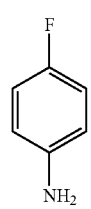
-continued
[873-74-5]
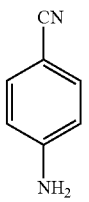
[63006-66-6]
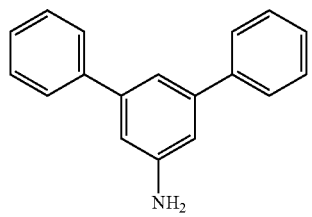
| Ex. | Starting material | Product | Yield |
|---|---|---|---|
| L1 | | | 38% |
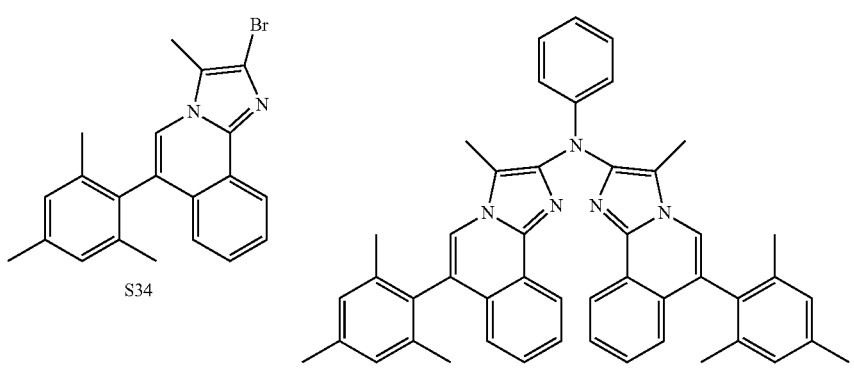
| L2 | | | 31% |
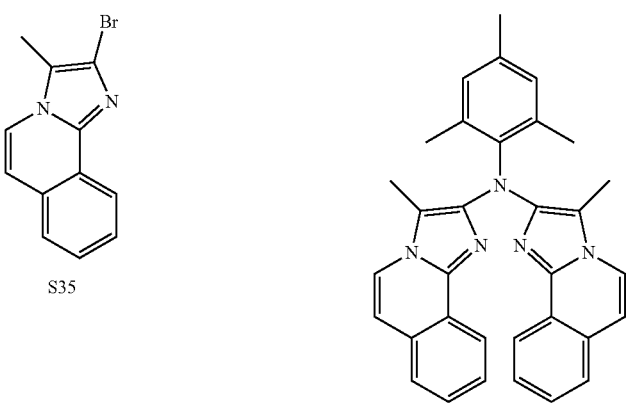

| Ex. | Starting material | Product | Yield |
|---|---|---|---|
| L3 | 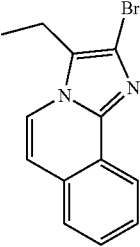<br>S36 | 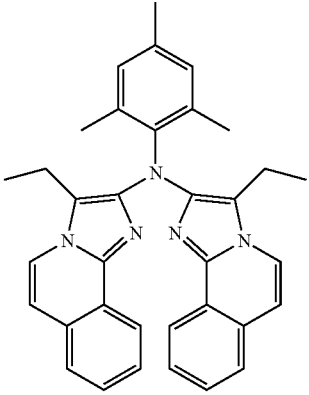 [SMILES: CCc1c(N(c2nc3c4ccccc4ccn3c2CC)c2c(C)cc(C)cc2C)nc2c3ccccc3ccn12] | 30% |
| L4 | 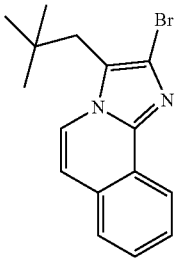<br>S37 | 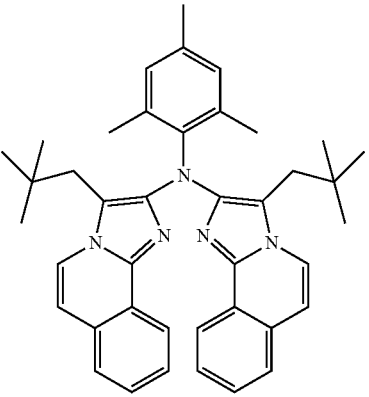 [SMILES: Cc1cc(C)c(N(c2nc3c4ccccc4ccn3c2CC(C)(C)C)c2nc3c4ccccc4ccn3c2CC(C)(C)C)c(C)c1] | 26% |
| L5 | 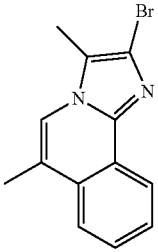<br>S38 | 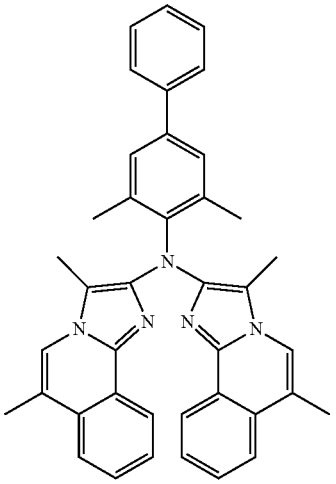 | 34% |

-continued
| Ex. | Starting material | Product | Yield |
|---|---|---|---|
| L6 | | | 44% |
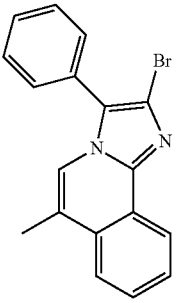
S39
| L7 | | | 30% |
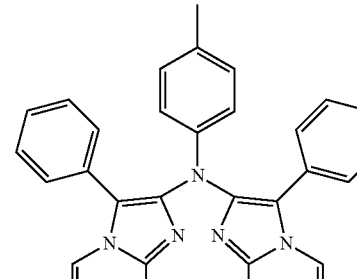
S40
| L8 | | | 41% |
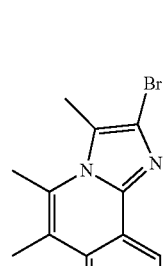
S41

| Ex. | Starting material | Product | Yield |
|---|---|---|---|
| L9 | 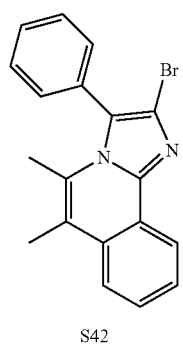 S42 | 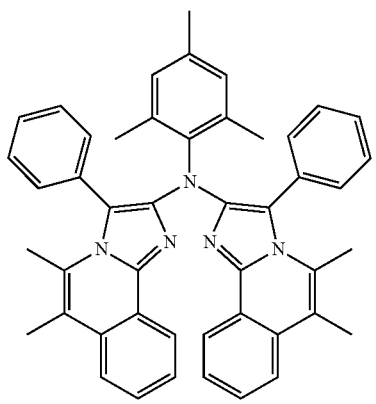 [SMILES: Cc1cc(C)c(N(c2nc3c4ccccc4c(C)c(C)n3c2-c2ccccc2)c2nc3c4ccccc4c(C)c(C)n3c2-c2ccccc2)c(C)c1] | 22% |
| L10 | 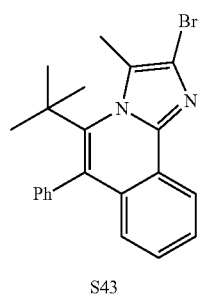 S43 | 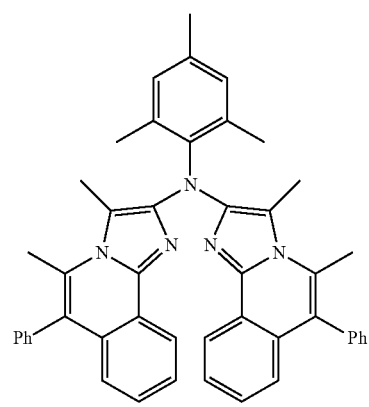 [SMILES: Cc1cc(C)c(N(c2nc3c4ccccc4c(-c4ccccc4)c(C)n3c2C)c2nc3c4ccccc4c(-c4ccccc4)c(C)n3c2C)c(C)c1] | 33% |
| L11 | 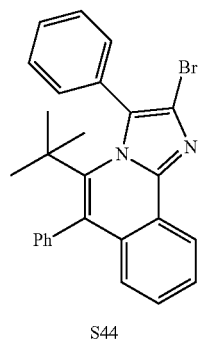 S44 | 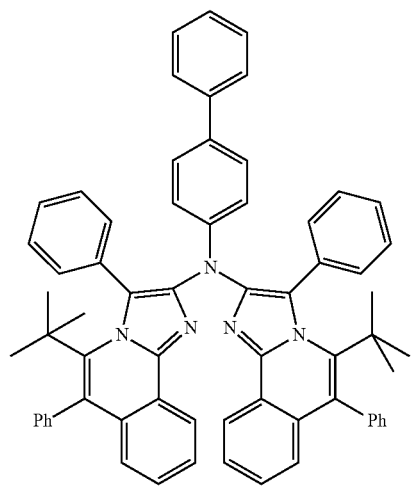 [SMILES: CC(C)(C)c1c(-c2ccccc2)c2ccccc2c2nc(N(c3ccc(-c4ccccc4)cc3)c3nc4c5ccccc5c(-c5ccccc5)c(C(C)(C)C)n4c3-c3ccccc3)c(-c3ccccc3)n12] | 30% |

| Ex. | Starting material | Product | Yield |
|---|---|---|---|
| L12 | S45 | | 36% |
| L13 | S46 | | 12% |
| L14 | S47 | | 27% |
| L15 | S48 | | 45% |
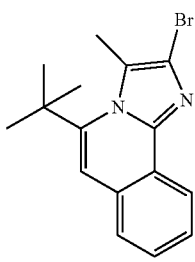
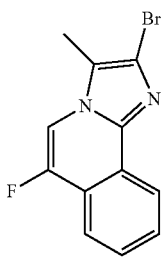
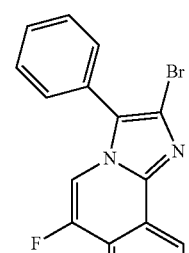
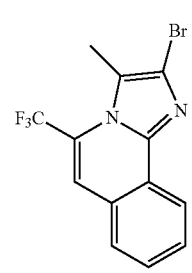

| Ex. | Starting material | Product | Yield |
|---|---|---|---|
| L16 | 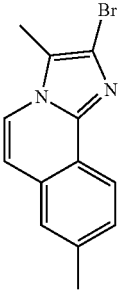\n\nS49 | 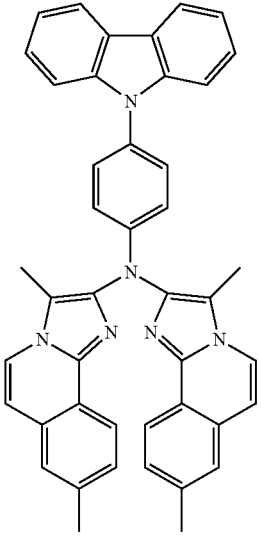 [SMILES: Cc1ccc2c(ccn3c(C)c(N(c4ccc(-n5c6ccccc6c6ccccc65)cc4)c4nc5c6ccc(C)cc6ccn5c4C)nc23)c1] | 46% |
| L17 | 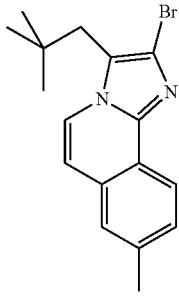\n\nS50 | 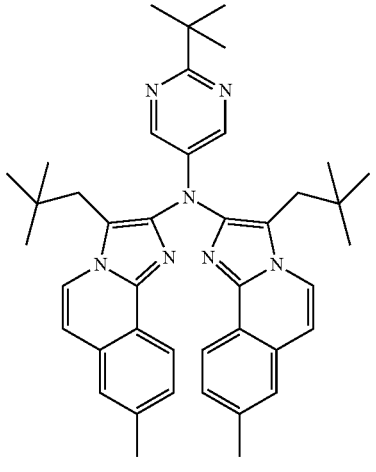 [SMILES: Cc1ccc2c(ccn3c(CC(C)(C)C)c(N(c4cnc(C(C)(C)C)nc4)c4nc5c6ccc(C)cc6ccn5c4CC(C)(C)C)nc23)c1] | 34% |
| L18 | 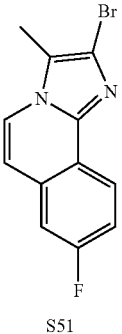\n\nS51 | 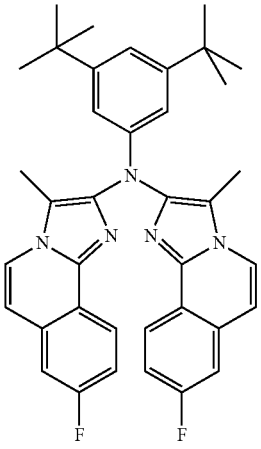 [SMILES: Cc1c(N(c2cc(C(C)(C)C)cc(C(C)(C)C)c2)c2nc3c4ccc(F)cc4ccn3c2C)nc2c3ccc(F)cc3ccn12] | 45% |

| Ex. | Starting material | Product | Yield |
|---|---|---|---|
| L19 | 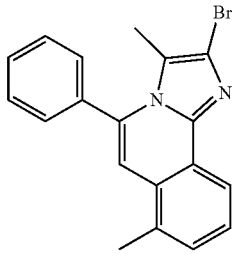<br>S52 | 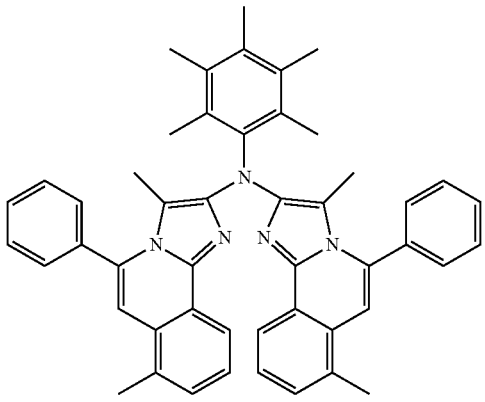 [SMILES: Cc1c(C)c(C)c(N(c2nc3c4cccc(C)c4cc(-c4ccccc4)n3c2C)c2nc3c4cccc(C)c4cc(-c4ccccc4)n3c2C)c(C)c1C] | 28% |
| L20 | 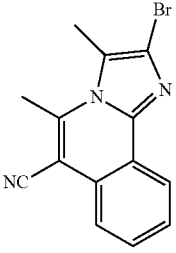<br>S53 | 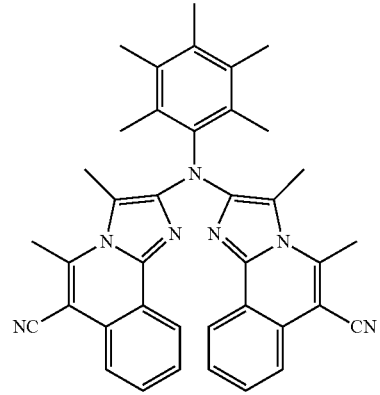 [SMILES: Cc1c(C)c(C)c(N(c2nc3c4ccccc4c(C#N)c(C)n3c2C)c2nc3c4ccccc4c(C#N)c(C)n3c2C)c(C)c1C] | 26% |
| L21 | 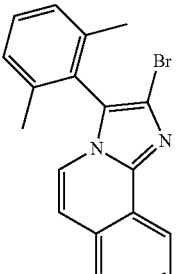<br>S54 | 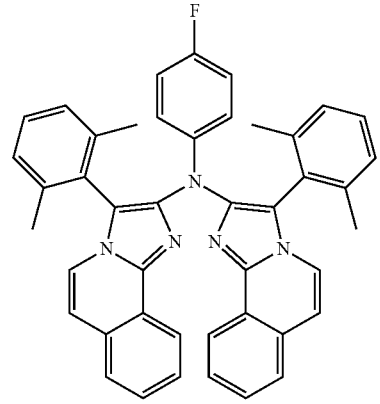 [SMILES: Cc1cccc(C)c1-c1c(N(c2ccc(F)cc2)c2nc3c4ccccc4ccn3c2-c2c(C)cccc2C)nc2c3ccccc3ccn12] | 43% |

| Ex. | Starting material | Product | Yield |
|---|---|---|---|
| L22 | 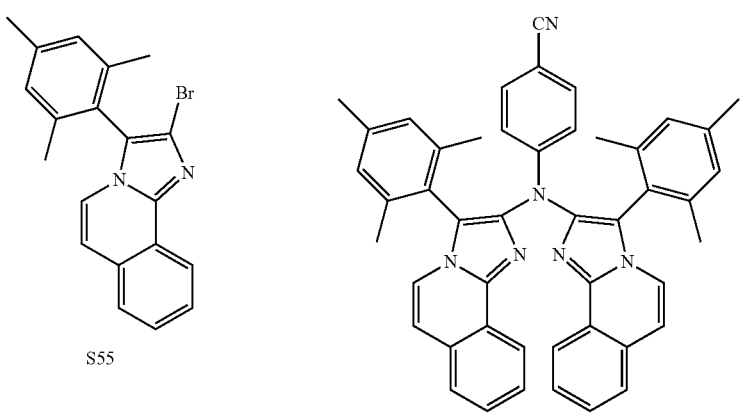 S55 | 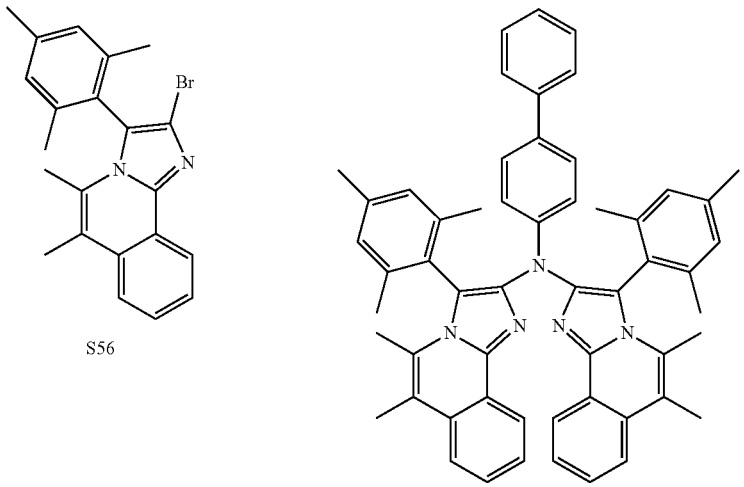 | 45% |
| L23 | 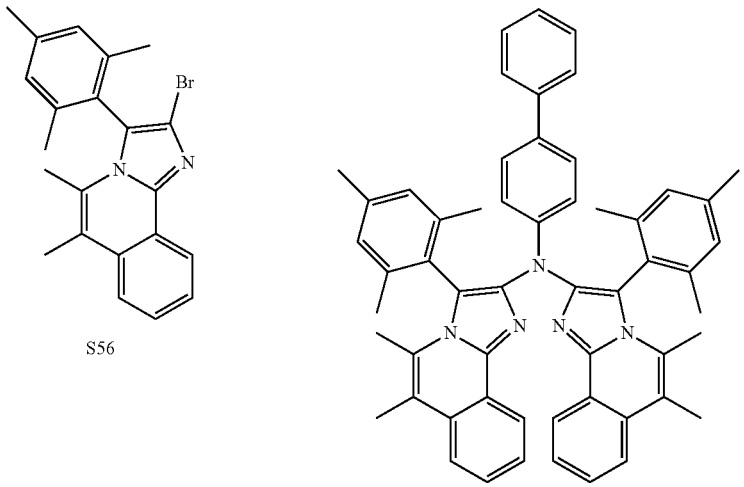 S56 | 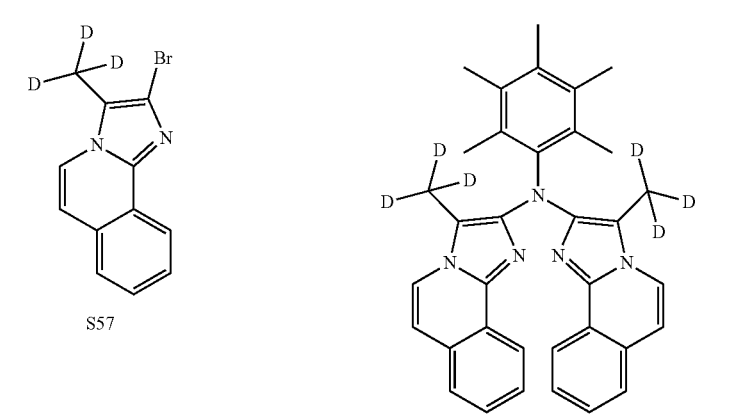 | 29% |
| L24 | 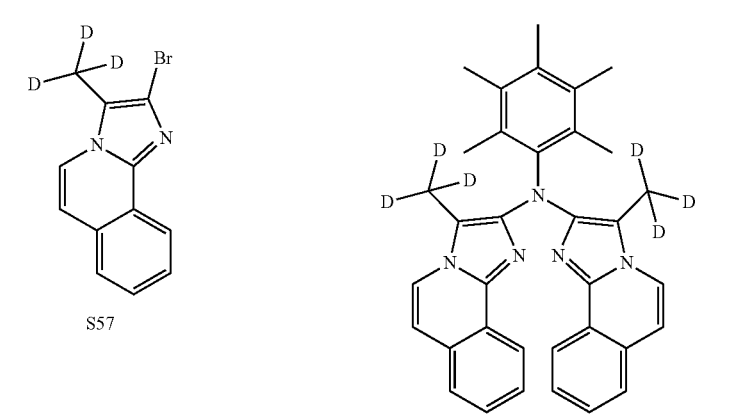 S57 | | 32% |

| Ex. | Starting material | Product | Yield |
|---|---|---|---|
| L25 | S58 | | 44% |
| L26 | S59 | | 35% |
| L27 | S60 | | 34% |

| Ex. | Starting material | Product | Yield |
|---|---|---|---|
| L28 | 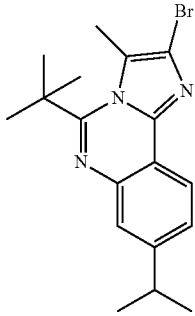 S61 | 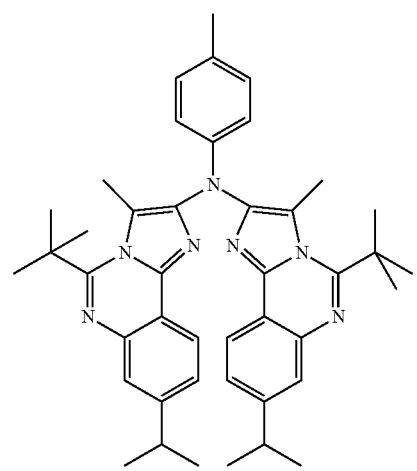 [SMILES: Cc1ccc(N(c2nc3c4ccc(C(C)C)cc4nc(C(C)(C)C)n3c2C)c2nc3c4ccc(C(C)C)cc4nc(C(C)(C)C)n3c2C)cc1] | 46% |
| L29 | 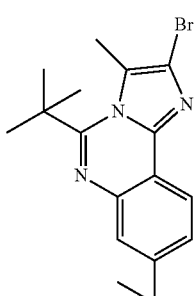 S62 | 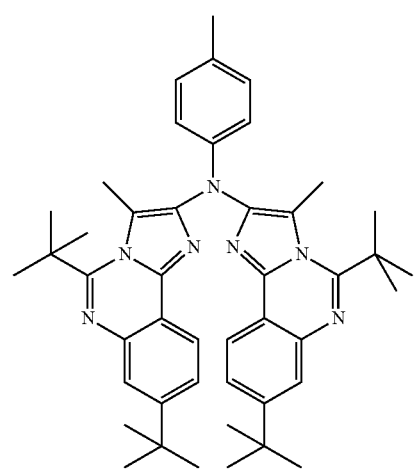 [SMILES: Cc1ccc(N(c2nc3c4ccc(C(C)(C)C)cc4nc(C(C)(C)C)n3c2C)c2nc3c4ccc(C(C)(C)C)cc4nc(C(C)(C)C)n3c2C)cc1] | 44% |
| L30 | 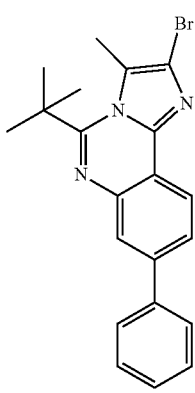 S63 | 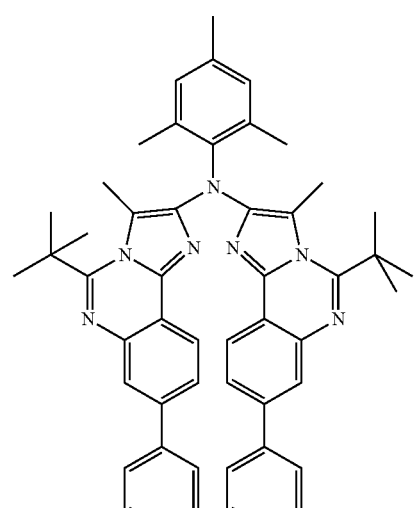 | 36% |

| Ex. | Starting material | Product | Yield |
|---|---|---|---|
| L31 | 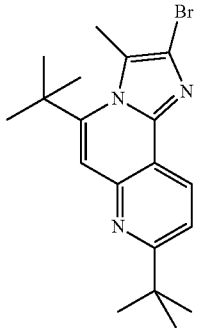
S64 | 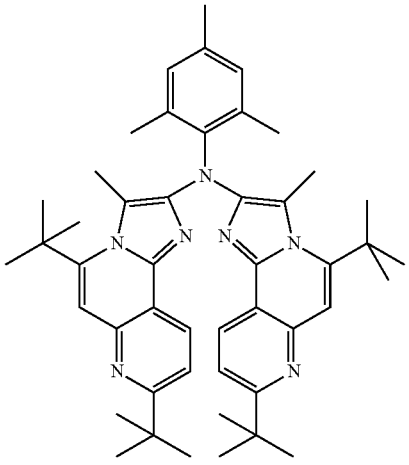 | 38% |
| L32 | 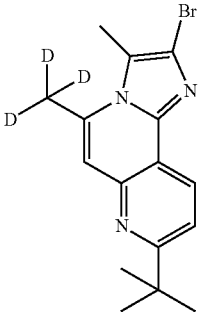
S65 | 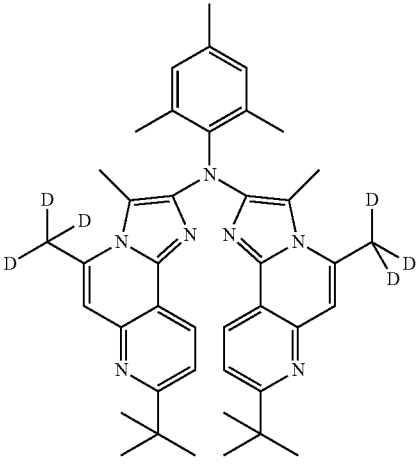 | 39% |
| L33 | 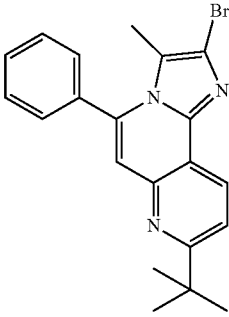
S66 | 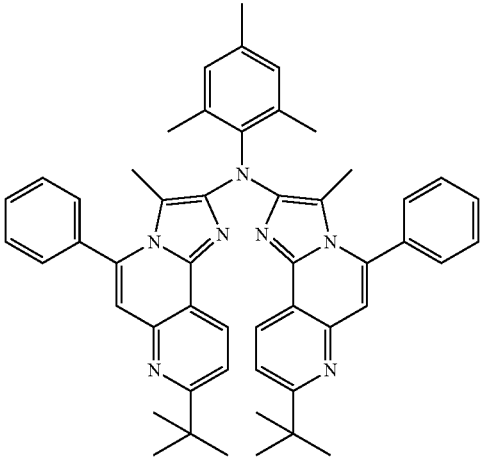 | 36% |

-continued

| Ex. | Starting material | Product | Yield |
|---|---|---|---|
| L34 | S67 | | 33% |
| L35 | S68 | | 32% |
| L36 | S69 | | 35% |

-continued
| Ex. | Starting material | Product | Yield |
|---|---|---|---|
| L37 | | | 30% |
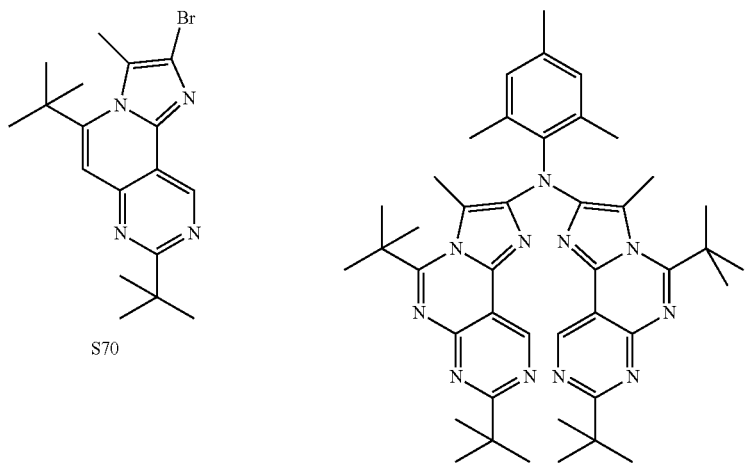
S70
| L38 | | | 48% |
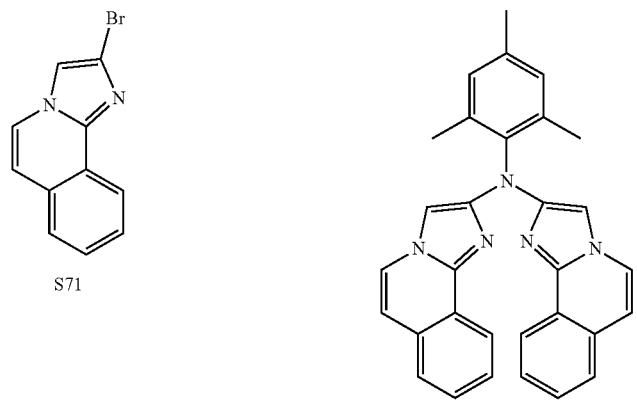
S71
| L39 | | | 45% |
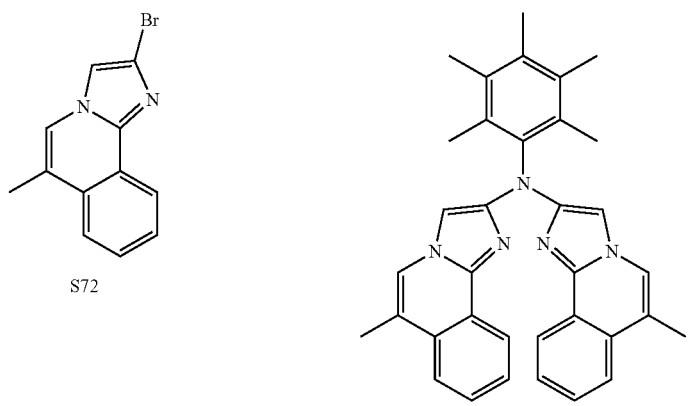
S72

| Ex. | Starting material | Product | Yield |
|---|---|---|---|
| L40 | 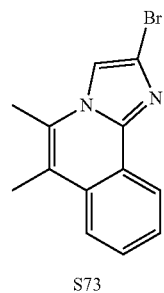 [SMILES: Cc1c(C)n2cc(Br)nc2c2ccccc12 ; "S73"]<br>S73 | 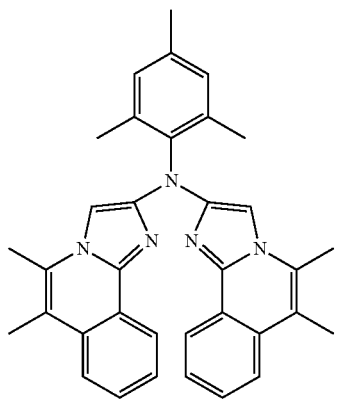 | 50% |
| L41 | 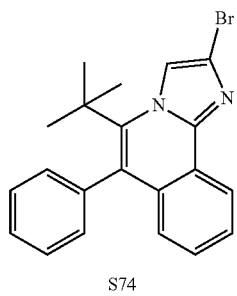 [SMILES: CC(C)(C)c1c(-c2ccccc2)c2ccccc2c2nc(Br)cn12 ; "S74"]<br>S74 | 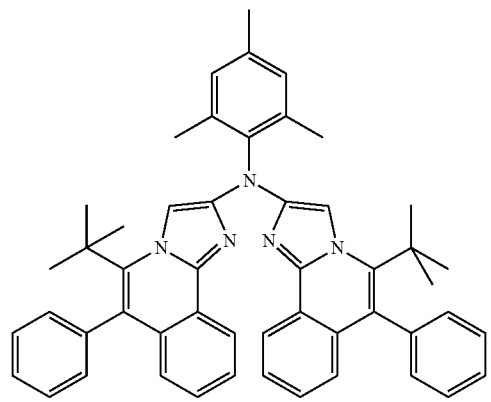 [SMILES: Cc1cc(C)c(N(c2cn3c(C(C)(C)C)c(-c4ccccc4)c4ccccc4c3n2)c2cn3c(C(C)(C)C)c(-c4ccccc4)c4ccccc4c3n2)c(C)c1] | 47% |
| L42 | 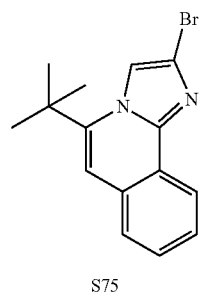 [SMILES: CC(C)(C)c1cc2ccccc2c2nc(Br)cn12 ; "S75"]<br>S75 | 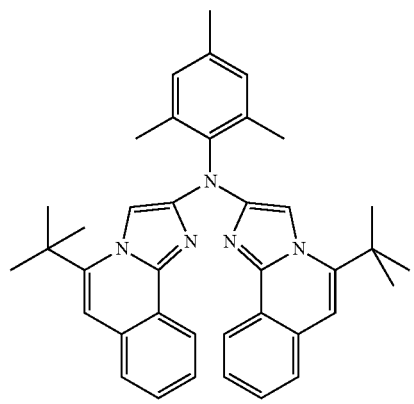 [SMILES: Cc1cc(C)c(N(c2cn3c(C(C)(C)C)cc4ccccc4c3n2)c2cn3c(C(C)(C)C)cc4ccccc4c3n2)c(C)c1] | 50% |

-continued
| Ex. | Starting material | Product | Yield |
|---|---|---|---|
| L43 | 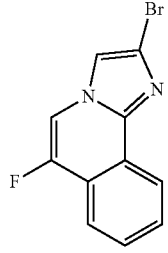<br>S76 | 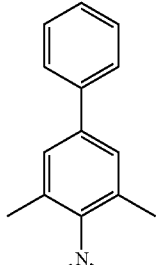 | 47% |
| L44 | 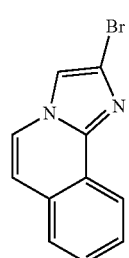<br>S77 | 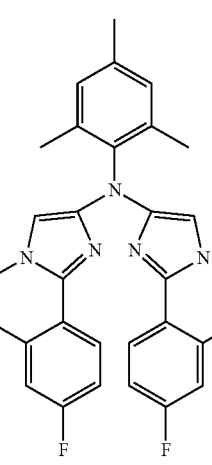 | 45% |
| L45 | 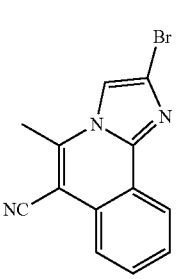<br>S78 | 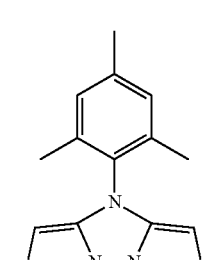 | 36% |

| Ex. | Starting material | Product | Yield |
|---|---|---|---|
| L46 | 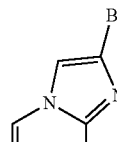 S79 | 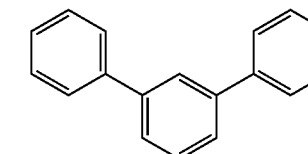 | 51% |

2) Ligands where V=BR 40.0 ml (100 mmol) of n-butyllithium, 2.5 M in N-hexane, are added dropwise to a solution, cooled to −78° C., of 100 mmol of the bromide in 300 ml of THF. The reaction mixture is stirred for a further 30 min., and a solution of 840 mg (50 mmol) of difluoromesitylborane in 100 ml of THF is then added dropwise. The reaction mixture is stirred at −78° C. for a further 1 h, then allowed to warm to room temperature, the THF is removed in vacuo, the residue is taken up in 300 ml of dichloromethane, washed twice with 100 ml of water each time, dried over sodium sulfate, the solvent is removed in vacuo, the oily residue is recrystallised from ethyl acetate/methanol, and the solid is subsequently freed from readily volatile and non-volatile components by fractional sublimation (p about $10^{-5}$ mbar, T about 260-300° C.). Purity: about 99% according to $^1$H-NMR.

| Ex. | Starting material | Product | Yield |
|---|---|---|---|
| L47 | 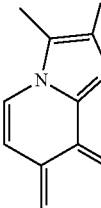 S35 | 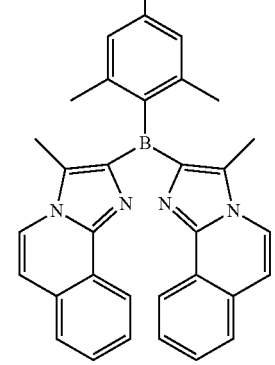 | 46% |
| L48 | 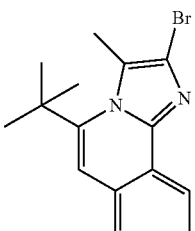 S45 | 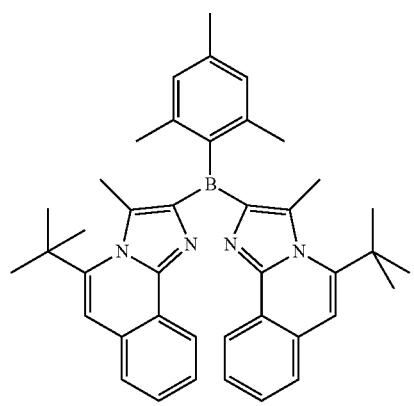 | 40% |

| Ex. | Starting material | Product | Yield |
|---|---|---|---|
| L49 | S58 | | 38% |

3) Ligands where V=O

A mixture of 100 mmol of the bromide, 4.0 g (100 mmol) of sodium hydroxide, 14.9 g (120 mmol) of n-butylimidazole, 26.4 g (100 mmol) of 18-crown-6 and 1.9 g (10 mmol) of copper(I) iodide in 200 ml of diethylene glycol dimethyl ether is heated at 120° C. for 16 h. After cooling, the reaction mixture is washed three times with 300 ml of water each time, dried over sodium sulfate, the solvent is removed in vacuo, the oily residue is recrystallised from ethyl acetate/methanol, and the solid is subsequently freed from readily volatile and non-volatile components by fractional sublimation (p about $10^{-5}$ mbar, T about 260-300° C.). Purity: about 99% according to $^1$H-NMR.

| Ex. | Starting material | Product | Yield |
|---|---|---|---|
| L50 | S35 | | 31% |
| L51 | S45 | | 38% |
| L52 | S58 | | 35% |

-continued

| Ex. | Starting material | Product | Yield |
|---|---|---|---|
| L53 | S64 | | 30% |
| L54 | S75 | | 37% |

C: Synthesis of Metal Complexes

A mixture of 10 mmol of bis(benzonitrile)platinum(II) dichloride and 10 mmol of the ligand L in 100 ml of benzonitrile is heated under reflux for 16 h. After dropwise addition of 100 ml of methanol to the cooled reaction mixture, the solid is filtered off with suction, washed five times with 25 ml of methanol each time and dried in vacuo. The solid is suspended in 100 ml of glacial acetic acid, 20 ml of pyridine and 1.5 g of zinc dust are added to the suspension, and the mixture is stirred at 90° C. for 5 h. After cooling, the solid is filtered off with suction, washed three times with 25 ml of methanol each time and dried in vacuo. The solid obtained in this way is placed in a hot extractor on a Celite bed with a depth of 3 cm and then extracted with toluene (introduced amount about 300 ml). When the extraction is complete, the extractant is evaporated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot extraction step is repeated; when a purity of 99.5-99.9% has been achieved, the Pt complex is sublimed. The sublimation is carried out in a high vacuum (p about $10^{-6}$ mbar) in the temperature range from about 320 to about 390° C., where the sublimation is preferably carried out in the form of a fractional sublimation.

| Ligand | Pt complex | Yield |
|---|---|---|
| L1 | PtL1 | 32% |
| L2 | PtL2 | 30% |
| L3 | PtL3 | 30% |
| L4 | PtL4 | 28% |
| L5 | PtL5 | 36% |
| L6 | PtL6 | 38% |
| L7 | PtL7 | 35% |
| L8 | PtL8 | 41% |
| L9 | PtL9 | 33% |
| L10 | PtL10 | 37% |
| L11 | PtL11 | 30% |
| L12 | PtL12 | 40% |
| L13 | PtL13 | 39% |
| L14 | PtL14 | 44% |
| L15 | PtL15 | 31% |
| L16 | PtL16 | 35% |
| L17 | PtL17 | 35% |
| L18 | PtL18 | 36% |
| L19 | PtL19 | 38% |
| L20 | PtL20 | 33% |
| L21 | PtL21 | 40% |
| L22 | PtL22 | 38% |
| L23 | PtL23 | 39% |
| L24 | PtL24 | 34% |

-continued

| Ligand | Pt complex | Yield |
|---|---|---|
| L25 | PtL25 | 35% |
| L26 | PtL26 | 33% |
| L27 | PtL27 | 35% |
| L28 | PtL28 | 35% |
| L29 | PtL29 | 36% |
| L30 | PtL30 | 38% |
| L31 | PtL31 | 40% |
| L32 | PtL32 | 41% |
| L33 | PtL33 | 40% |
| L34 | PtL34 | 35% |
| L35 | PtL35 | 34% |
| L36 | PtL36 | 33% |
| L37 | PtL37 | 34% |
| L38 | PtL38 | 39% |
| L39 | PtL39 | 45% |
| L40 | PtL40 | 44% |
| L41 | PtL41 | 45% |
| L42 | PtL42 | 47% |
| L43 | PtL43 | 44% |
| L44 | PtL44 | 45% |
| L45 | PtL45 | 43% |
| L46 | PtL46 | 46% |
| L47 | | 27% |

PtL47

| L48 | PtL48 | 23% |
| L49 | PtL49 | 25% |
| L50 | | 38% |

PtL50

| L51 | PtL51 | 40% |
| L52 | PtL52 | 43% |
| L53 | PtL53 | 39% |
| L54 | PtL54 | 40% |

Example

Production of OLEDs

OLEDs according to the invention and OLEDs in accordance with the prior art are produced by a general process in accordance with WO 2004/058911, which is adapted to the circumstances described here (layer-thickness variation, materials used).

The results for various OLEDs are presented in the following examples (see Tables 1 and 2). Glass plates which have been coated with structured ITO (indium tin oxide) in a thickness of 150 nm are coated with 20 nm of PEDOT (poly(3,4-ethylenedioxy-2,5-thiophene), applied by spin-coating from water; purchased from H. C. Starck, Goslar, Germany) for improved processing. These coated glass plates form the substrates to which the OLEDs are applied. The OLEDs have in principle the following layer structure: substrate/optional hole-injection layer (HIL1)/optional hole-injection layer (HIL2)/hole-transport layer (HTL)/electron-blocking layer (EBL)/emission layer (EML)/optional hole-blocking layer (HBL)/electron-transport layer (ETL) and finally a cathode. The cathode is formed by an aluminium layer with a thickness of 100 nm Firstly, vacuum-processed OLEDs are described. For this purpose, all materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as M1:M2:PtL (55%:35%:10%) here means that material M1 is present in the layer in a proportion by volume of 55%, M2 is present in the layer in a proportion of 35% and PtL is present in the layer in a proportion of 10%. Analogously, the electron-transport layer may also consist of a mixture of two materials. The precise structure of the OLEDs is shown in Table 1. The materials used for the production of the OLEDs are shown in Table 3.

The OLEDs are characterised by standard methods. For this purpose, the electroluminescence spectra, the current efficiency (measured in cd/A) and the voltage (measured at 1000 cd/m$^2$ in V) are determined from current/voltage/luminance characteristic lines (IUL characteristic lines). For selected experiments, the lifetime is determined. The lifetime is defined as the time after which the luminous density has dropped to a certain proportion from a certain initial luminous density. The expression LT50 means that the lifetime given is the time at which the luminous density has dropped to 50% of the initial luminous density, i.e. from, for example, 4000 cd/m$^2$ to 2000 cd/m$^2$. Depending on the emission colour, different initial luminances were selected. The values for the lifetime can be converted to a figure for other initial luminous densities with the aid of conversion formulae known to the person skilled in the art. The lifetime for an initial luminous density of 1000 cd/m$^2$ is a usual figure here.

Use of Compounds According to the Invention as Emitter Materials in Phosphorescent OLEDs The compounds according to the invention can be employed, inter alia, as phosphorescent emitter materials in the emission layer in OLEDs. In the OLEDs, it is evident here that the materials according to the invention result in efficient blue- to green-emitting OLEDs.

TABLE 1

Use of compounds according to the invention as emitters in phosphorescent OLEDs

| Ex. | HIL1 Thickness | HIL2 Thickness | HTL Thickness | EML Thickness | HBL Thickness | ETL Thickness |
|---|---|---|---|---|---|---|
| 1 comp. | HIL1 20 nm | HIL3 5 nm | HTL1 15 nm | M1:HIL1:Pt-Vgl. (80%:10%:10%) 40 nm | M1 10 nm | ETM1:LiQ (50%:50%) 20 nm |
| 2 | HIL1 20 nm | HIL3 5 nm | HTL1 15 nm | M1:HIL1:PtL42 (80%:10%:10%) 40 nm | M1 10 nm | ETM1:LiQ (50%:50%) 20 nm |
| 3 | HIL1 80 nm | HIL2 10 nm | HTL2 20 nm | M1:PtL25 (90%:10%) 40 nm | ETM1 5 nm | ETM1:LiQ (50%:50%) 25 nm |
| 4 | HIL1 80 nm | HIL2 10 nm | HTL2 20 nm | M1:M2:PtL31 (20%:70%:10%) 40 nm | ETM1 5 nm | ETM1:LiQ (50%:50%) 25 nm |
| 5 | HIL1 80 nm | HIL2 10 nm | HTL2 20 nm | M1:M2:PtL54 (60%:40%:10%) 40 nm | ETM1 5 nm | ETM1:LiQ (50%:50%) 25 nm |

TABLE 2

Use of compounds according to the invention as emitters in phosphorescent OLEDs

| Ex. | EQE [%] at 1000 cd/m$^2$ | Voltage (V) at 1000 cd/m$^2$ | CIE x/y at 1000 cd/m$^2$ | LT50 (h) at 1000 cd/m$^2$ |
|---|---|---|---|---|
| 1 | 16.1 | 5.1 | 0.19/0.24 | 1100 |
| 2 | 16.4 | 4.7 | 0.17/0.23 | 1500 |
| 3 | 15.3 | 4.5 | 0.16/0.25 | 1400 |
| 4 | 12.2 | 5.6 | 0.15/0.16 | 600 |
| 5 | 15.0 | 5.0 | 0.15/0.22 | 800 |

TABLE 3

Structural formulae of the materials used

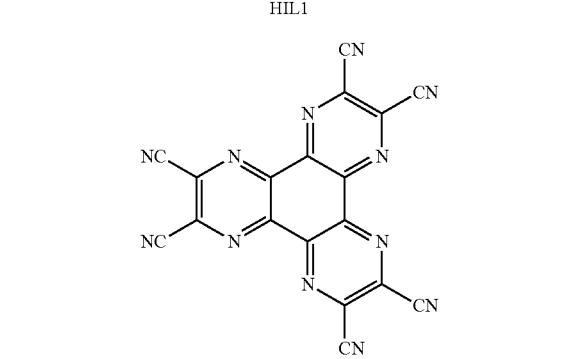

HIL1

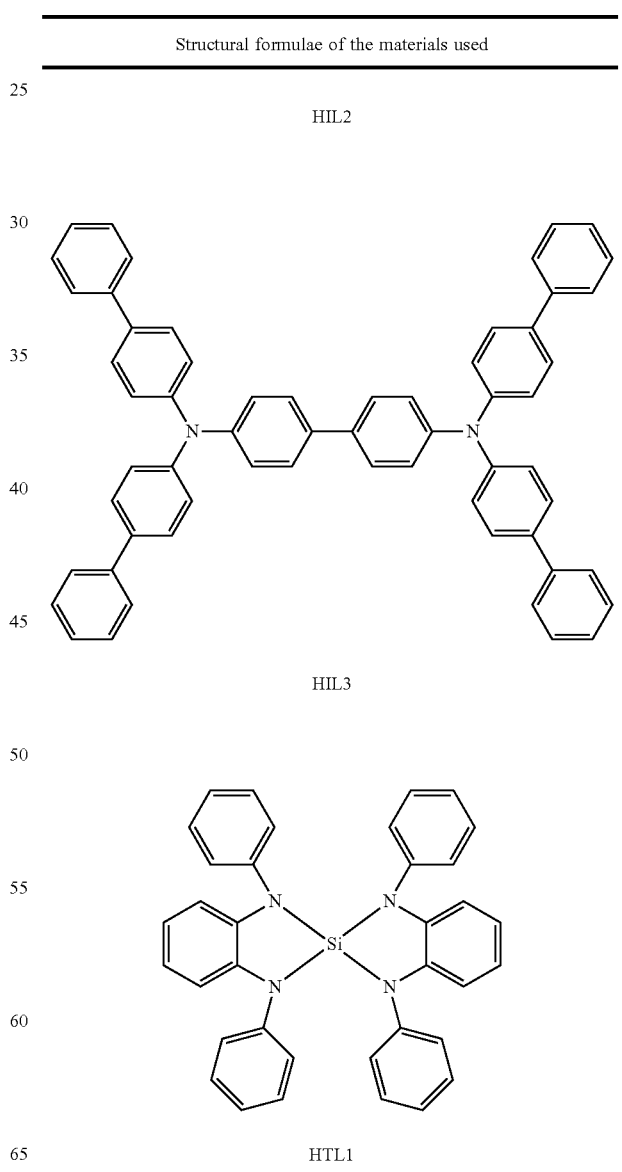

TABLE 3-continued

Structural formulae of the materials used

HIL2

HIL3

HTL1

TABLE 3-continued
Structural formulae of the materials used
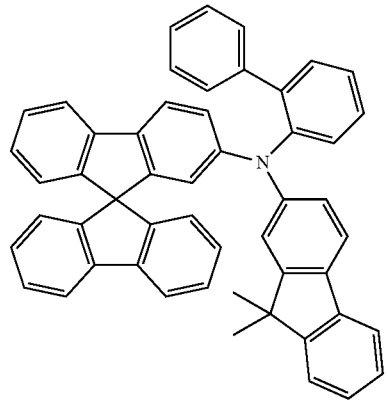 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HTL2
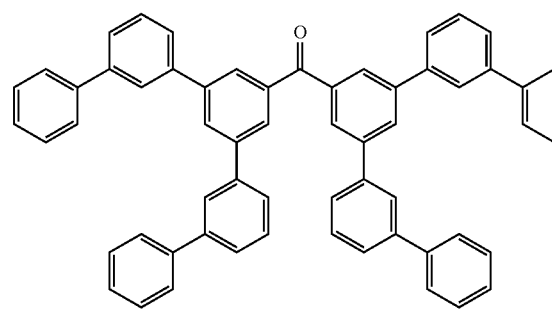
M1
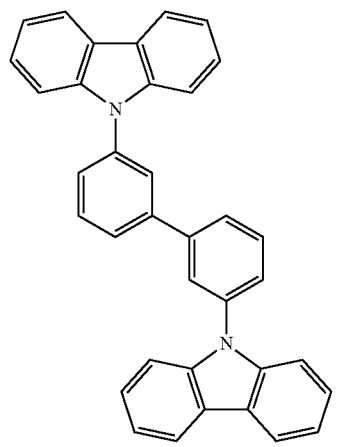 [SMILES: c1cc(-c2cccc(-n3c4ccccc4c4ccccc43)c2)cc(-n2c3ccccc3c3ccccc32)c1]
M2
TABLE 3-continued
Structural formulae of the materials used
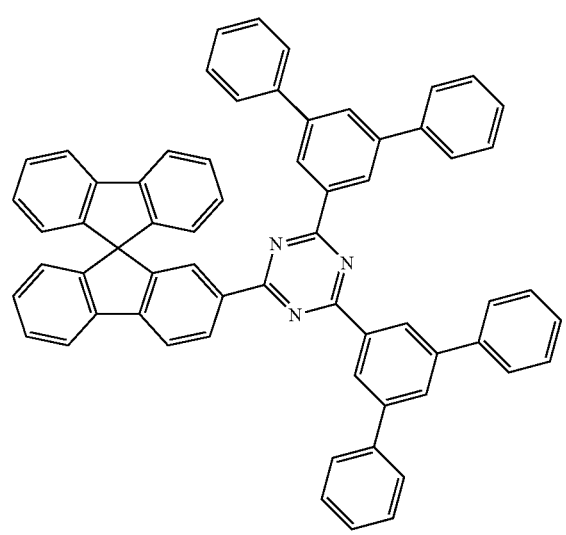 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM1
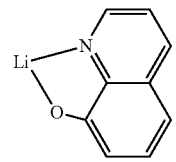
LiQ
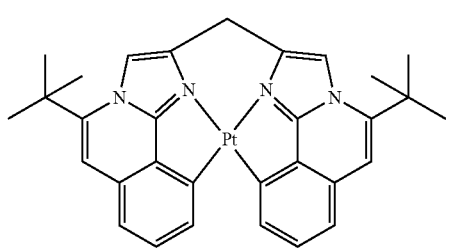
in accordance with WO 2010/086089
Comparison: Pt comp.
The invention claimed is:
1. A compound of formula (1),
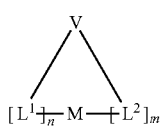
formula (1)
where $L^1$ stands, identically or differently on each occurrence, for a part-ligand of the following formula (2),

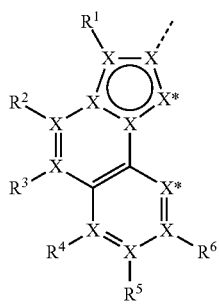

formula (2)

where the dashed bond indicates the bond to V, * denotes the position of the coordination to M and the following applies to the symbols and indices used:

M is Pt;

V is for NR$^7$ or O wherein when V is selected from NR$^7$, L$^1$ and L$^2$ are directly bonded to N, R$^7$ is of the formula (39) or (40)

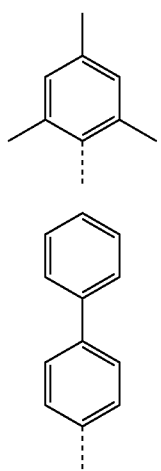

formula (39)

formula (40)

where the dashed bond represents the bond to the nitrogen atom,

X is on each occurrence, identically or differently, C or N, where all X in the part-ligand of the formula (2) together form a 14π electron system, with the proviso that at least two groups X and at most 6 groups X in each part-ligand of the formula (2) stand for N;

R$^1$ to R$^6$ is on each occurrence, identically or differently, H, D, F, Cl, Br, I, N(R$^8$)$_2$, CN, NO$_2$, Si(R$^8$)$_3$, B(OR$^8$)$_2$, C(=O)R$^8$, P(=O)(R$^8$)$_2$, S(=O)R$^8$, S(=O)$_2$R$^8$, OSO$_2$R$^8$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals R$^8$, where one or more non-adjacent CH$_2$ groups is optionally replaced by R$^8$C=CR$^8$, C≡C, Si(R$^8$)$_2$, C=O, C=S, C=NR$^8$, P(=O)(R$^8$), SO, SO$_2$, NR$^8$, O, S or CONR$^8$ and where one or more H atoms is optionally replaced by D, F, Cl, Br, I or CN, or an aromatic or heteroaromatic ring system having 5 to 60 aromatic ring atoms, which may in each case be substituted by one or more radicals R$^8$, or an aryloxy or heteroaryloxy group having 5 to 60 aromatic ring atoms, which is optionally substituted by one or more radicals R$^8$, or an aralkyl or heteroaralkyl group having 5 to 60 aromatic ring atoms, which is optionally substituted by one or more radicals R$^8$, or a diarylamino group, diheteroarylamino group or arylheteroarylamino group having 10 to 40 aromatic ring atoms, which is optionally substituted by one or more radicals R$^8$; R$^4$ and R$^5$ and/or R$^5$ and R$^6$ and/or R$^1$ and R$^7$ here may also form a mono- or polycyclic, aliphatic, aromatic and/or benzo-fused ring system with one another; furthermore, R$^2$ and R$^3$ may form a mono- or polycyclic, aliphatic ring system with one another; with the proviso that R$^1$ to R$^6$ represents a free electron pair if the group X to which this radical R$^1$ to R$^6$ is bonded is a nitrogen atom with a saturated valence;

R$^8$ is on each occurrence, identically or differently, H, D, F, Cl, Br, I, N(R$^9$)$_2$, CN, NO$_2$, Si(R$^9$)$_3$, B(OR$^9$)$_2$, C(=O)R$^9$, P(=O)(R$^9$)$_2$, S(=O) R$^9$, S(=O)$_2$R$^9$, OSO$_2$R$^9$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals R$^9$, where one or more non-adjacent CH$_2$ groups is optionally replaced by R$^9$C=CR$^9$, C≡C, Si(R$^9$)$_2$, C=O, C=S, C=NR$^9$, P(=O)(R$^9$), SO, SO$_2$, NR$^9$, O, S or CONR$^9$ and where one or more H atoms is optionally replaced by D, F, Cl, Br, I or CN, or an aromatic or heteroaromatic ring system having 5 to 60 aromatic ring atoms, which may in each case be substituted by one or more radicals R$^9$, or an aryloxy or heteroaryloxy group having 5 to 60 aromatic ring atoms, which is optionally substituted by one or more radicals R$^9$, or an aralkyl or heteroaralkyl group having 5 to 60 aromatic ring atoms, which is optionally substituted by one or more radicals R$^9$, or a diarylamino group, diheteroarylamino group or arylheteroarylamino group having 10 to 40 aromatic ring atoms, which is optionally substituted by one or more radicals R$^9$; two or more adjacent radicals R$^8$ here may form a mono- or polycyclic, aliphatic or aromatic ring system with one another;

R$^9$ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents R$^9$ here may also form a mono- or polycyclic, aliphatic or aromatic ring system with one another;

L$^2$ is a bidentate part-ligand which is bonded to V;

n is 1 or 2; and m is (2−n).

2. The compound according to claim 1, wherein the part-ligand of the formula (2) is selected from structures of the formula (4),

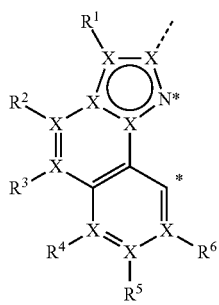

formula (4)

where the symbols used have the meanings given in claim 1 and at least one symbol X and at most 5 symbols X stand for N.

3. The compound according to claim 2, wherein V is NR$^7$ and R$^7$ is of the formula (39).

4. The compound according to claim 2, wherein V is NR$^7$ and R$^7$ is of the formula (40).

5. The compound according to claim 2, wherein V is O.

6. The compound according to claim 1, wherein the part-ligand of the formula (2) is selected from the part-ligands of the formulae (5), (6) or (7),

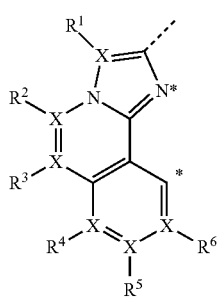

formula (5)

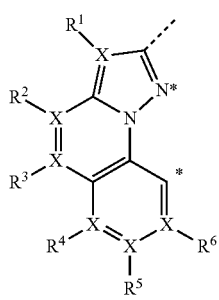

formula (6)

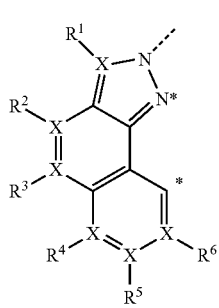

formula (7)

where the symbols used have the meanings given in claim 1, in the case of the use of the part-ligands of the formula (7) the bridging unit V is selected from BR$^7$ and B(R$^7$)$_2$ and the part-ligands contain two, three, four, five or six nitrogen atoms.

7. The compound according to claim 1, wherein the part-ligands of the formula (2) are selected from the part-ligands of the formulae (5a) to (5r), (6a) to (6r) or (7a) to (7r),

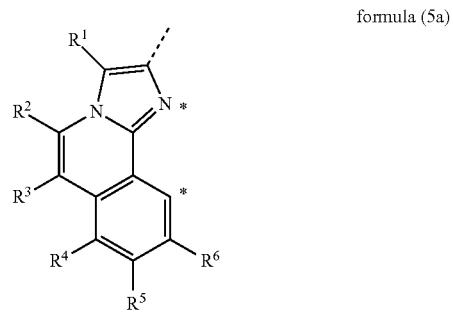

formula (5a)

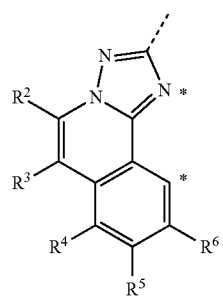

formula (5b)

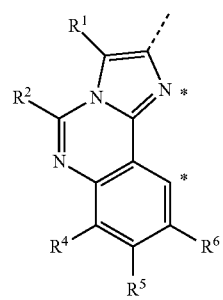

formula (5c)

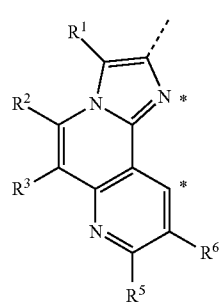

formula (5d)

formula (5e)
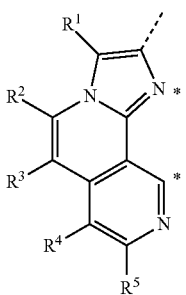
formula (5f)
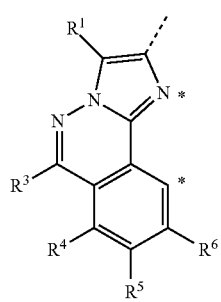
formula (5g)
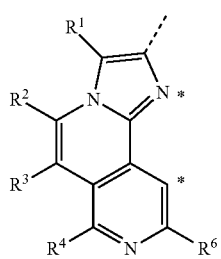
formula (5h)
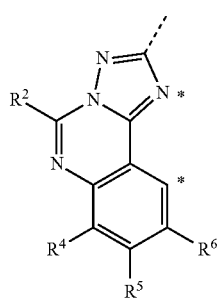
formula (5i)
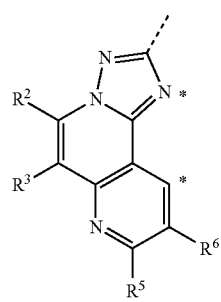
formula (5j)
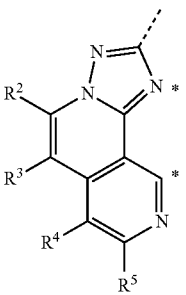
formula (5k)
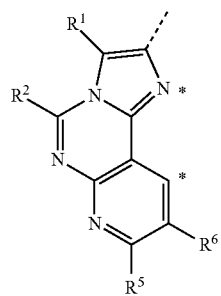
formula (5l)
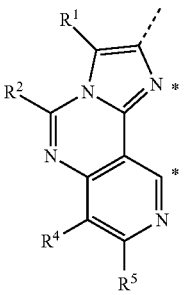
formula (5m)
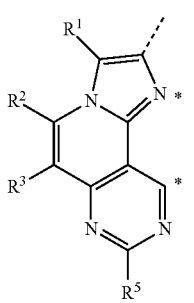
formula (5n)
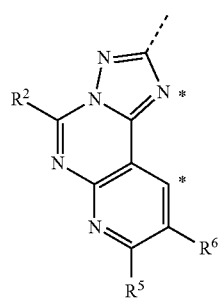

-continued
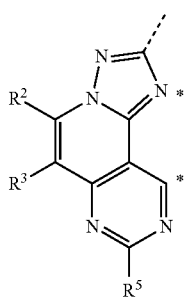
formula (5o)
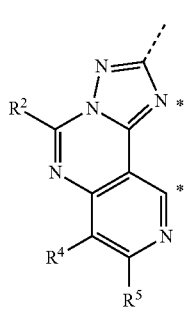
formula (5p)
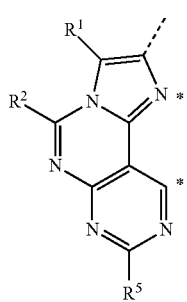
formula (5q)
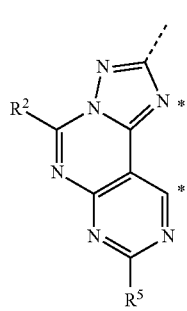
formula (5r)
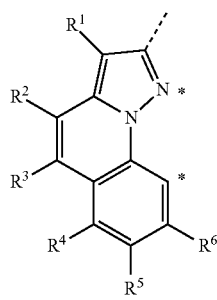
formula (6a)
-continued
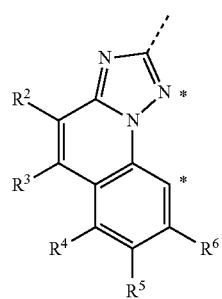
formula (6b)
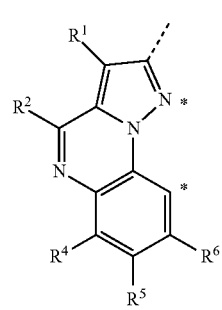
formula (6c)
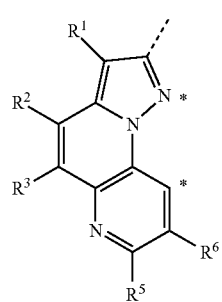
formula (6d)
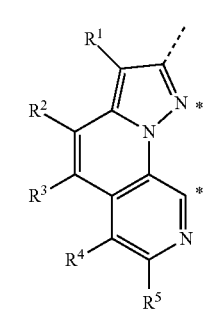
formula (6e)
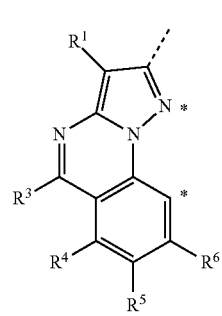
formula (6f)

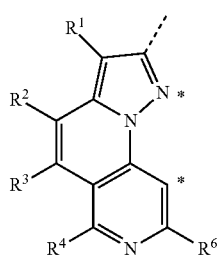 formula (6g)
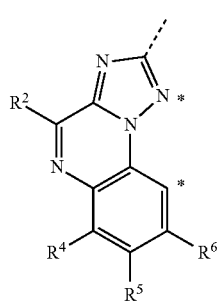 formula (6h)
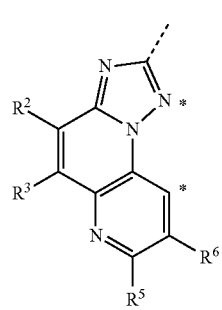 formula (6i)
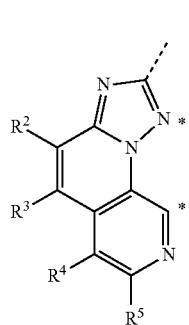 formula (6j)
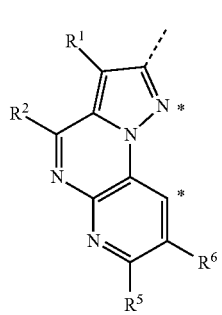 formula (6k)
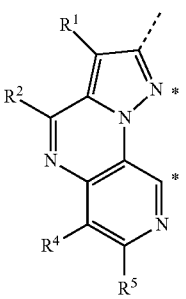 formula (6l)
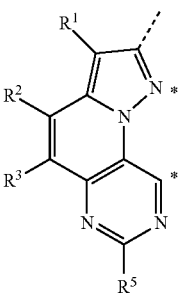 formula (6m)
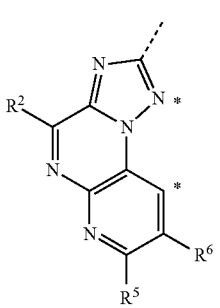 formula (6n)
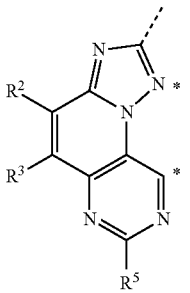 formula (6o)
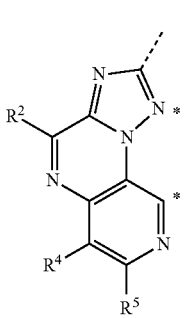 formula (6p)

formula (6q)
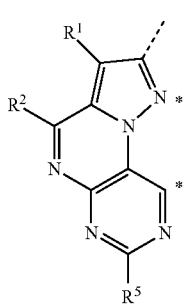
formula (6r)
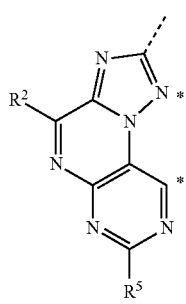
formula (7a)
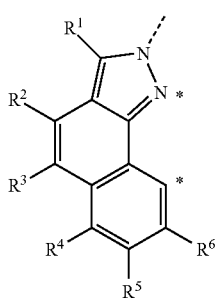
formula (7b)
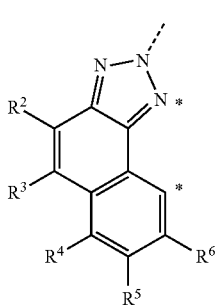
formula (7c)
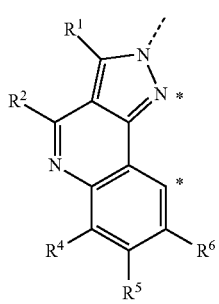
formula (7d)
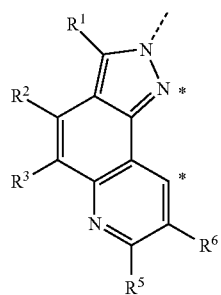
formula (7e)
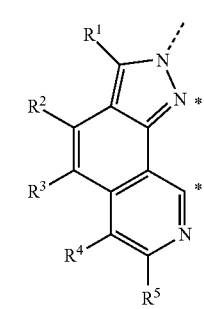
formula (7f)
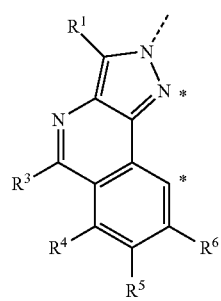
formula (7g)
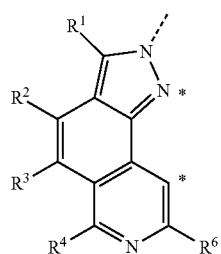
formula (7h)
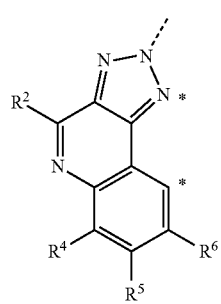

-continued formula (7i)
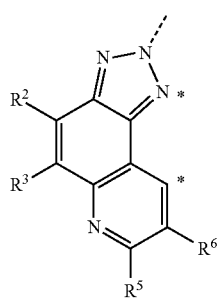

formula (7j)
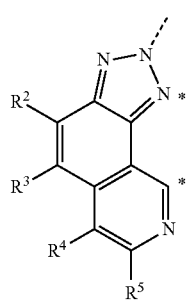

formula (7k)
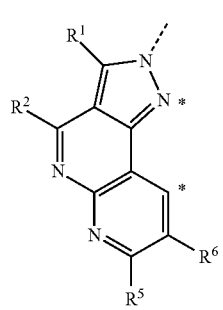

formula (7l)
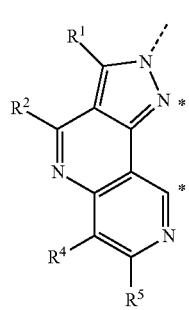

formula (7m)
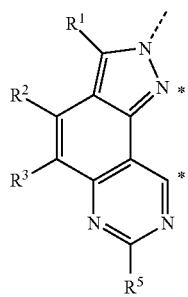

-continued formula (7n)
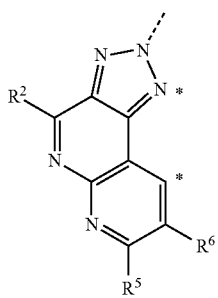

formula (7o)
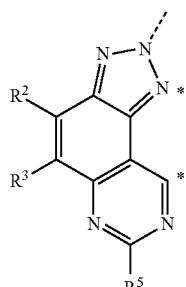

formula (7p)
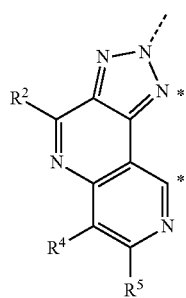

formula (7q)
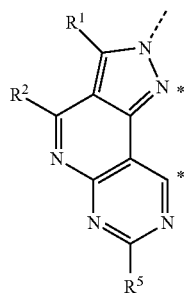

formula (7r)
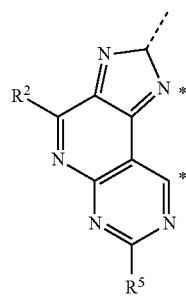

where the symbols used have the meanings given in claim 1.

8. The compound according to claim 1, wherein, if the part-ligand of the formula (2) contains 3 or more nitrogen atoms, a bulky radical which is selected, identically or differently on each occurrence, from the group consisting of N(R⁸)₂, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals R⁸, where one or more non-adjacent CH₂ groups is optionally replaced by R⁸C=CR⁸, C≡C, Si(R⁸)₂, C=O, C=S, C=NR⁸, P(=O)(R⁷), SO, SO₂, NR⁸, O, S or CONR⁸ and where one or more H atoms is optionally replaced by D, F, Cl, Br, I or CN, or an aromatic or heteroaromatic ring system having 5 to 60 aromatic ring atoms, which may in each case be substituted by one or more radicals R⁸, or an aryloxy or heteroaryloxy group having 5 to 60 aromatic ring atoms, which is optionally substituted by one or more radicals R⁸, or an aralkyl or heteroaralkyl group having 5 to 60 aromatic ring atoms, which is optionally substituted by one or more radicals R⁸, or a diarylamino group, diheteroarylamino group or arylheteroarylamino group having 10 to 40 aromatic ring atoms, which is optionally substituted by one or more radicals R⁸, is bonded to a carbon atom which is adjacent to a nitrogen atom which is not coordinated to the metal and which is not simultaneously bonded in a five-membered ring and a six-membered ring.

9. The compound according to claim 8, wherein the bulky radical is selected from the structures of the formulae (R-1) to (R-112):

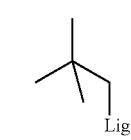
(R-1)

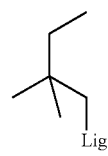
(R-2)

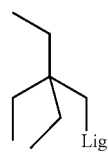
(R-3)

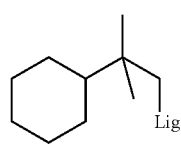
(R-4)

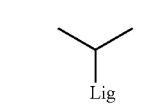
(R-5)

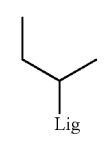
(R-6)

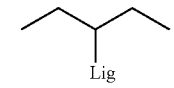
(R-7)

-continued

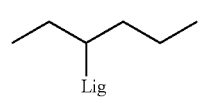
(R-8)

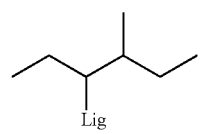
(R-9)

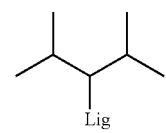
(R-10)

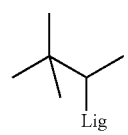
(R-11)

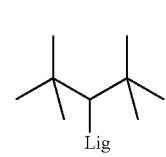
(R-12)

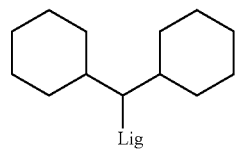
(R-13)

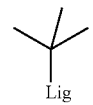
(R-14)

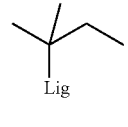
(R-15)

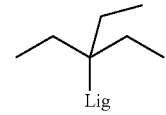
(R-16)

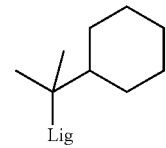
(R-17)

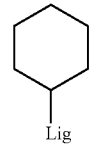
(R-18)

-continued
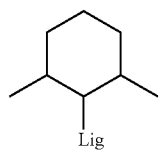 (R-19)
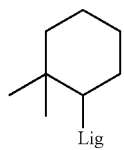 (R-20)
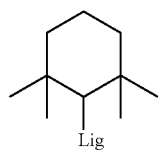 (R-21)
 (R-22)
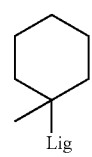 (R-23)
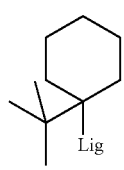 (R-24)
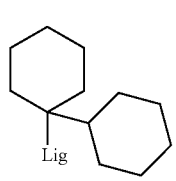 (R-25)
 (R-26)
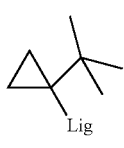 (R-27)
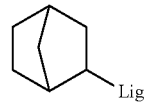 (R-28)
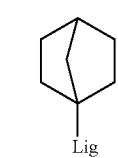 (R-29)
-continued
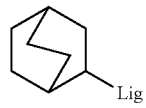 (R-30)
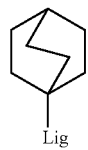 (R-31)
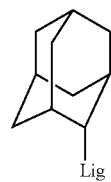 (R-32)
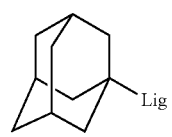 (R-33)
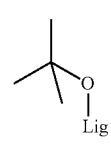 (R-34)
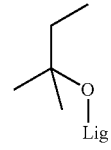 (R-35)
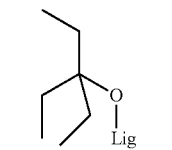 (R-36)
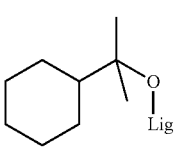 (R-37)
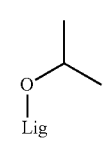 (R-38)
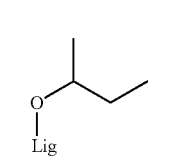 (R-39)

-continued
(R-40) 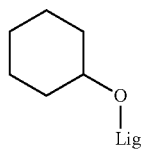
(R-41) 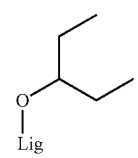
(R-42) 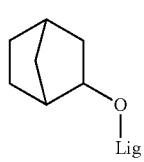
(R-43) 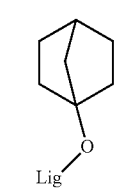
(R-44) 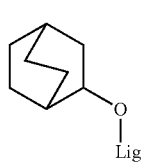
(R-45) 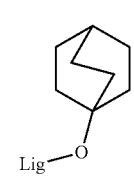
(R-46) 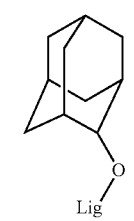
(R-47) 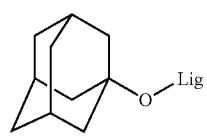
(R-48) 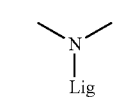
(R-49) 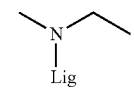
-continued
(R-50) 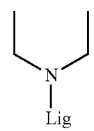
(R-51) 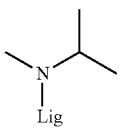
(R-52) 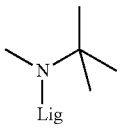
(R-53) 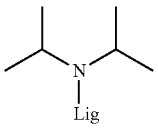
(R-54) 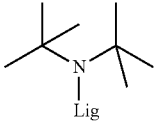
(R-55) 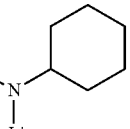
(R-56) 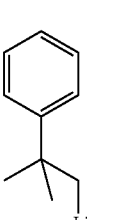
(R-57) 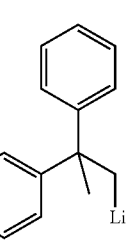
(R-58) 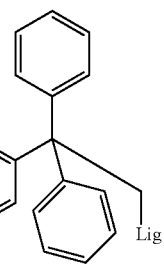

-continued
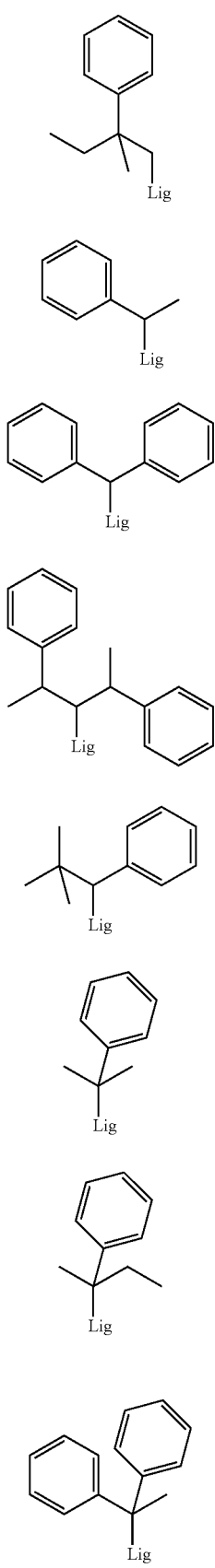
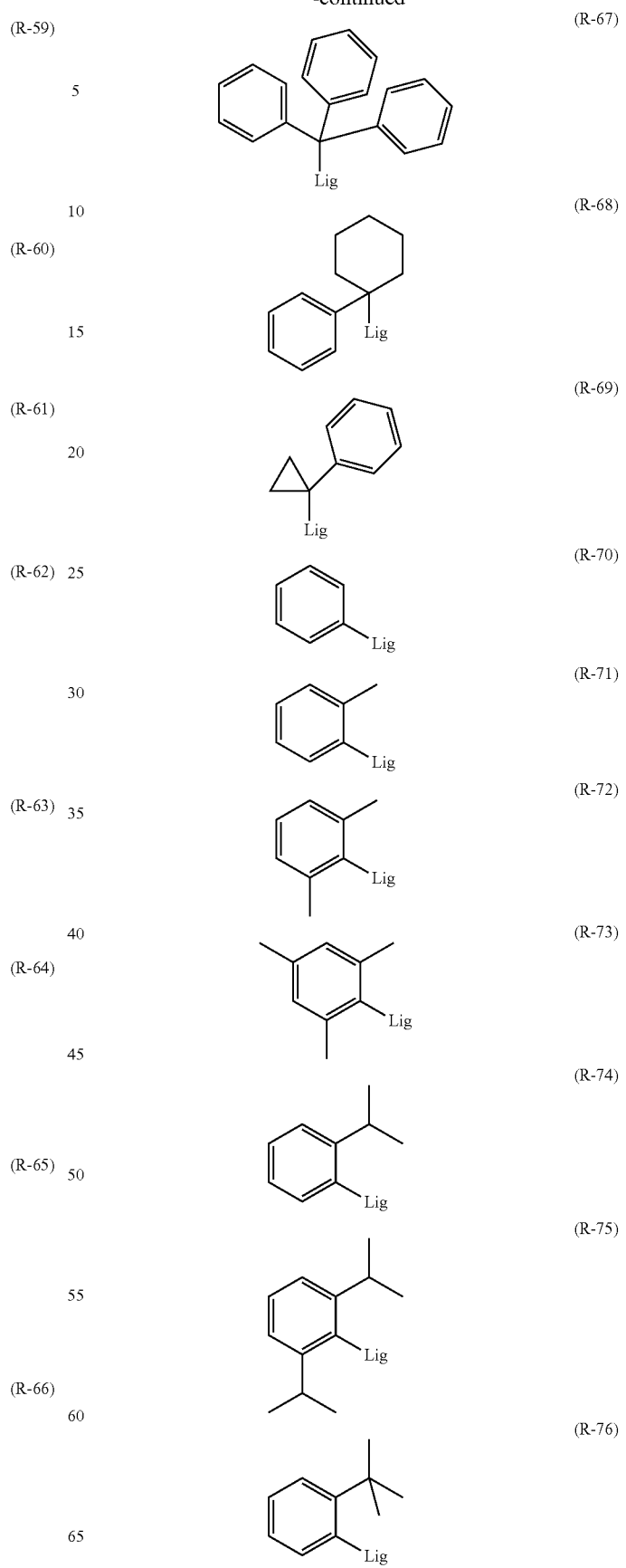

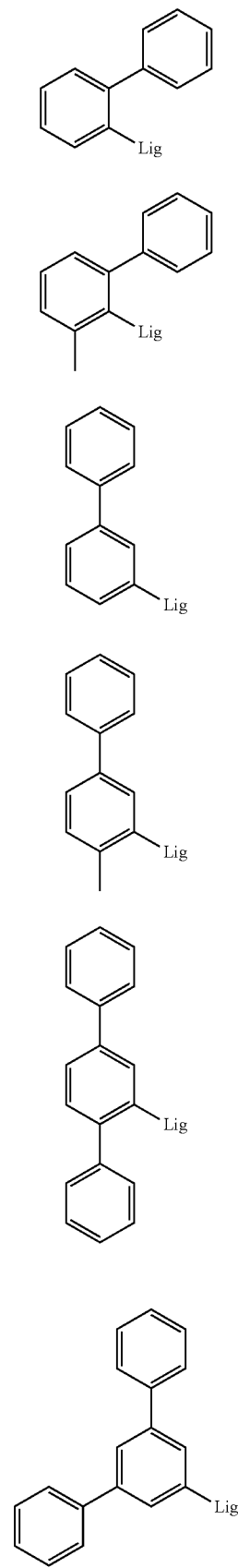
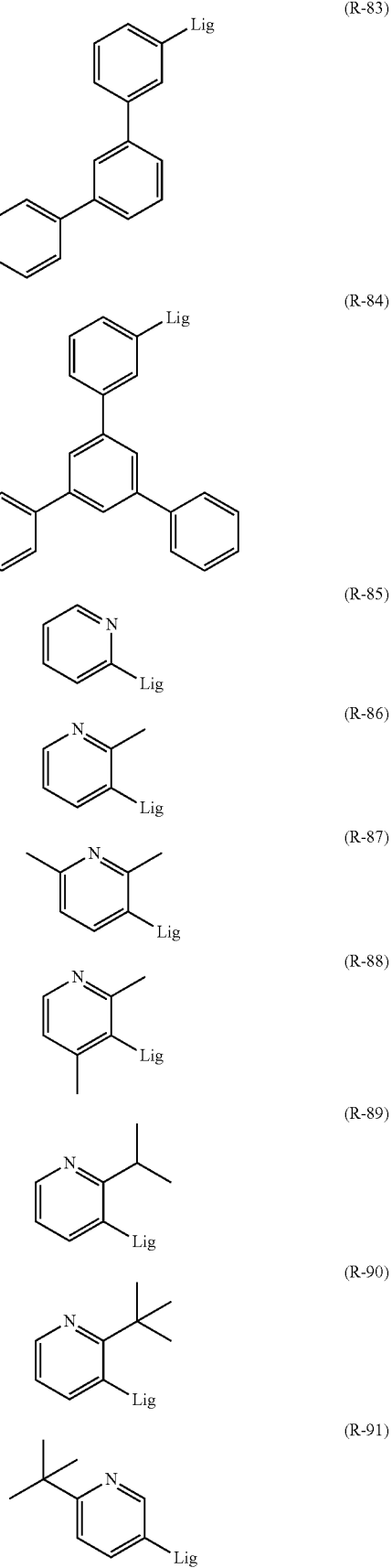

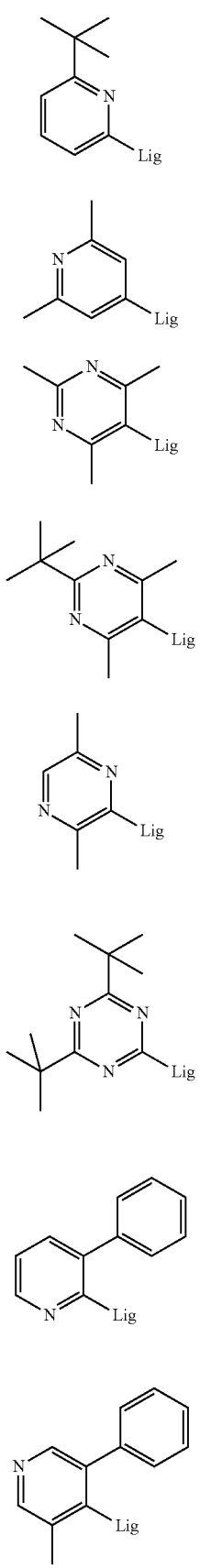
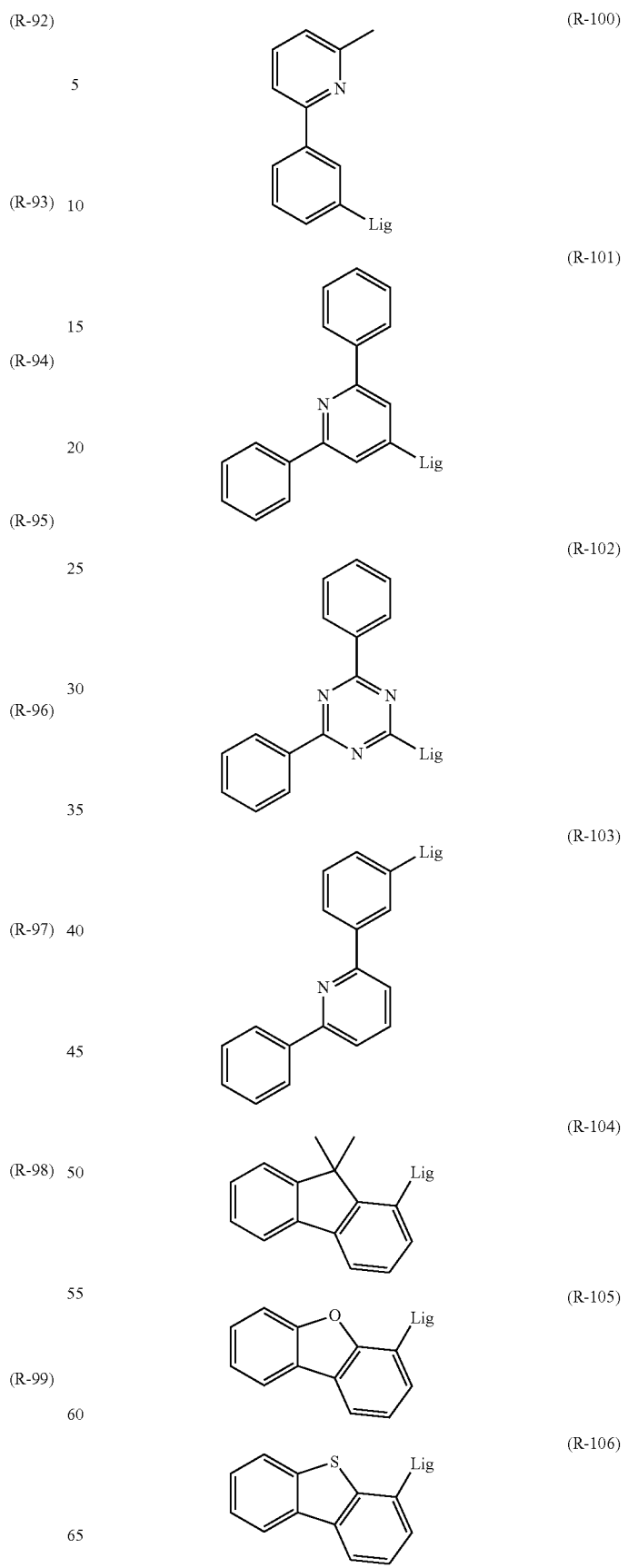

-continued

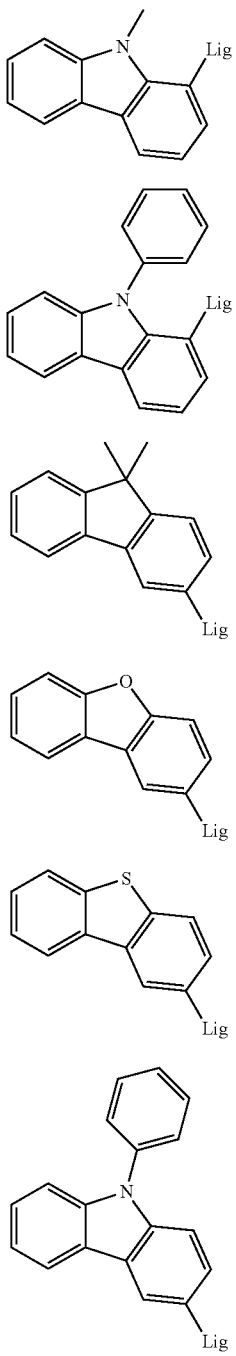

(R-107)

(R-108)

(R-109)

(R-110)

(R-111)

(R-112)

where Lig denotes the link from the group to the ligand and the aromatic and heteroaromatic groups may each be substituted by one or more radicals $R^8$.

10. The compound according to claim 1, wherein the index n=2 and the two part-ligands of the formula (2) are identical.

11. The compound according to claim 1, wherein V stands for $NR^7$.

12. A process for the preparation of the compound according to claim 1 which comprises reacting the corresponding free ligand with metal alkoxides of the formula (46), with metal ketoketonates of the formula (47) or with metal halides of the formula (48),

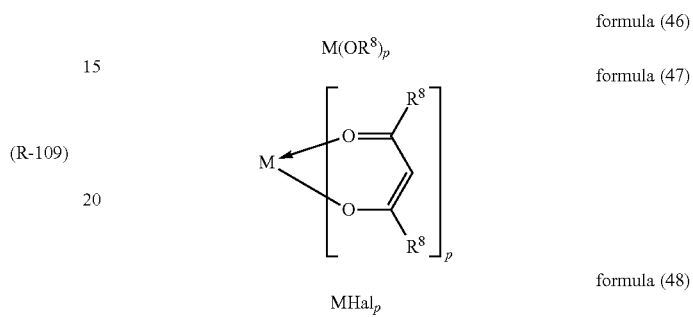

formula (46)
$$M(OR^8)_p$$

formula (47)

formula (48)
$$MHal_p$$

where the symbols M and $R^8$ have the meanings indicated in claim 1, Hal=F, Cl, Br or I and p stands for 1, 2 or 3, depending on the valence of the metal M.

13. A formulation comprising one or more compounds according to claim 1 and at least one solvent.

14. The formulation as according to claim 13, wherein the formulation is a solution, suspension or mini-emulsion.

15. An electronic device which comprises the compound according to claim 1.

16. The electronic device as claimed in claim 15, wherein the electronic device is selected from the group consisting of an organic electroluminescent device, an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell or an organic laser diode.

17. An organic electroluminescent device which comprises the compound according to claim 1 as emitting compound in one or more emitting layers.

18. An electronic device which comprises the compound according to claim 1 is employed in combination with a matrix material which is selected from the group consisting of ketones, phosphine oxides, sulfoxides, sulfones, triarylamines, carbazole derivatives, indolocarbazole derivatives, indenocarbazole derivatives, azacarbazoles, bipolar matrix materials, azaboroles, boronic esters, diazasilole derivatives, diazaphosphole derivatives, triazine derivatives, zinc complexes, dibenzofuran derivatives or bridged carbazole derivatives.

* * * * *